(12) United States Patent
Alvarez et al.

(10) Patent No.: US 12,115,294 B2
(45) Date of Patent: Oct. 15, 2024

(54) SYSTEMS AND METHODS FOR EXPRESSION OF BREAST MILK

(71) Applicant: WILLOW INNOVATIONS, INC., Mountain View, CA (US)

(72) Inventors: Janica B. Alvarez, Redwood City, CA (US); Kris Hoglund, Palo Alto, CA (US); Nathaniel Gaskin, Palo Alto, CA (US); Polina A. Segalova, Redwood City, CA (US); Jeffery B. Alvarez, Redwood City, CA (US)

(73) Assignee: Willow Innovations, Inc., Mountain View, CA (US)

( * ) Notice: Subject to any disclaimer, the term of this patent is extended or adjusted under 35 U.S.C. 154(b) by 751 days.

(21) Appl. No.: 16/909,007

(22) Filed: Jun. 23, 2020

(65) Prior Publication Data

US 2020/0316274 A1    Oct. 8, 2020

Related U.S. Application Data

(63) Continuation of application No. 15/829,779, filed on Dec. 1, 2017, now Pat. No. 10,702,640.

(60) Provisional application No. 62/429,657, filed on Dec. 2, 2016.

(51) Int. Cl.
*A61M 1/06* (2006.01)
*A61M 1/00* (2006.01)

(52) U.S. Cl.
CPC ............ *A61M 1/066* (2014.02); *A61M 1/062* (2014.02); *A61M 1/064* (2014.02); *A61M 1/82* (2021.05); *A61M 2205/0205* (2013.01); *A61M 2205/84* (2013.01); *A61M 2209/086* (2013.01)

(58) Field of Classification Search
CPC ...... A61M 1/066; A61M 1/062; A61M 1/064; A61M 1/82; A61M 2205/0205; A61M 2205/84; A61M 2209/086; A61M 2205/583

See application file for complete search history.

(56) References Cited

U.S. PATENT DOCUMENTS

| | | | | |
|---|---|---|---|---|
| 10,702,640 B2 * | 7/2020 | Alvarez | ................ | A61M 1/066 |
| 2002/0198489 A1 * | 12/2002 | Silver | ................... | A61M 1/064 |
| | | | | 119/14.47 |
| 2006/0106346 A1 * | 5/2006 | Sullivan | ............ | A61M 5/14586 |
| | | | | 604/82 |
| 2007/0060873 A1 * | 3/2007 | Hiraoka | ................. | A61M 1/82 |
| | | | | 604/74 |

(Continued)

*Primary Examiner* — Amber R Stiles

(57) ABSTRACT

Disclosed herein are improved devices, systems, and methods for the expression and collection of breast milk, such as human breast milk. A breast shield assembly for expression of breast milk may comprise a breast interface and an actuatable assembly interface fluidly coupled with a tube, wherein the breast interface is configured to engage the breast and the actuatable assembly interface is configured to removably couple to an actuatable assembly. The breast shield assembly may comprise an enclosed fluid reservoir extending between the breast interface and the actuatable assembly interface, the fluid reservoir physically separated from the expressed breast milk and filled with a driving fluid comprising a liquid. The breast shield assembly may further comprise a fill port configured to allow addition or removal of the driving fluid to or from the fluid reservoir.

20 Claims, 21 Drawing Sheets

(56) References Cited

U.S. PATENT DOCUMENTS

2008/0139998 A1\* 6/2008 Silver .................. A61M 1/066
604/74

\* cited by examiner

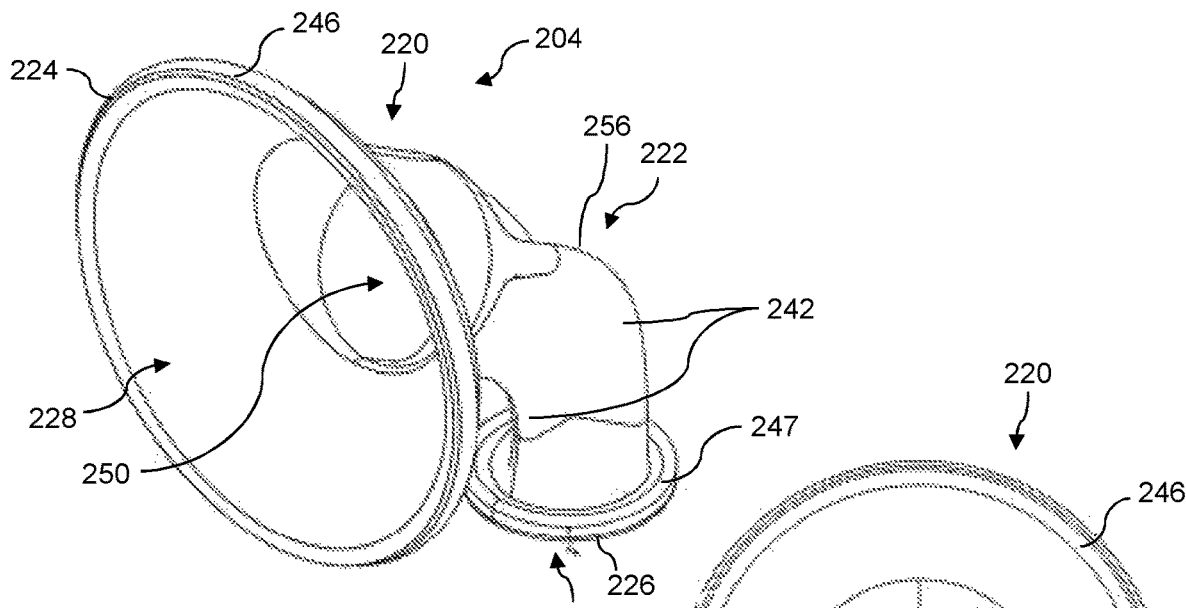
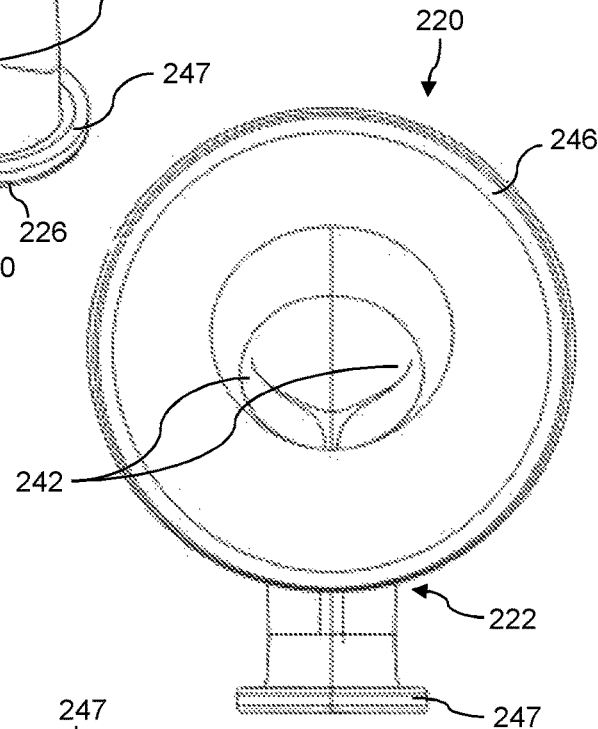
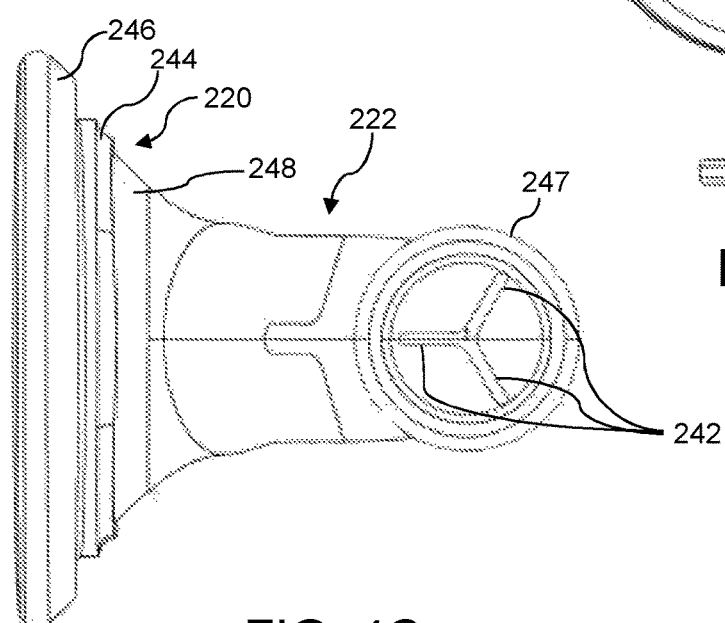
FIG. 4A
FIG. 4B
FIG. 4C

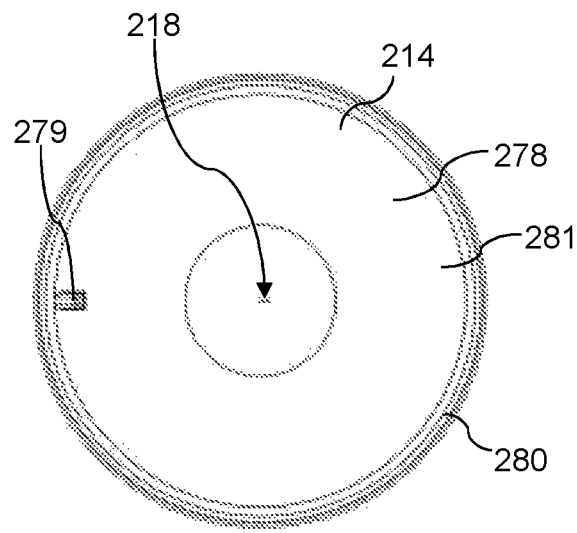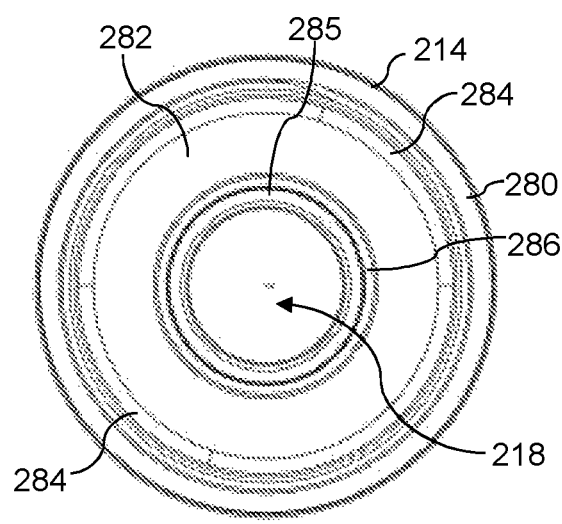
FIG. 7A    FIG. 7B
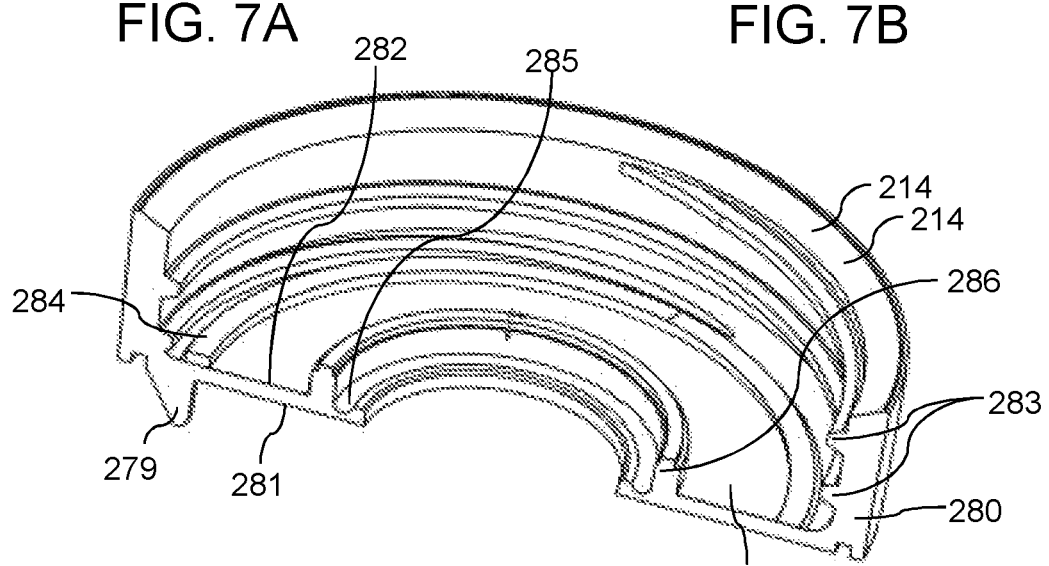
FIG. 7C
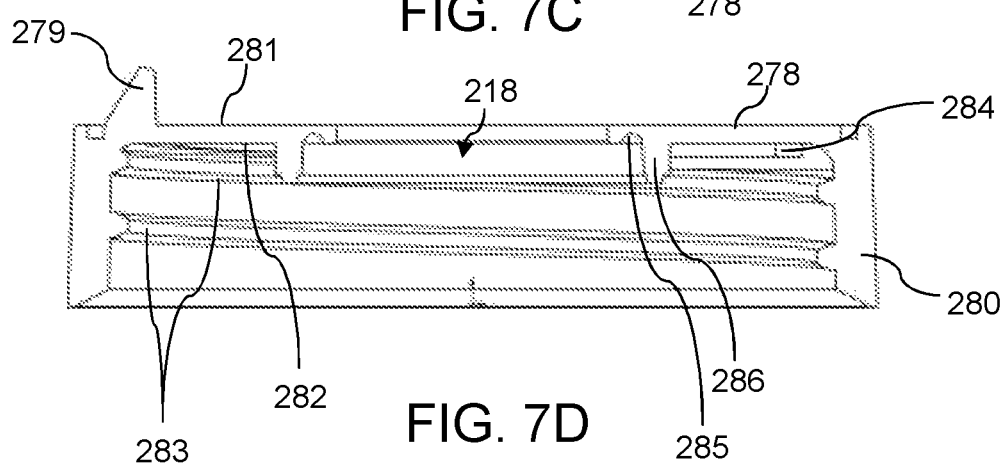
FIG. 7D

SYSTEMS AND METHODS FOR EXPRESSION OF BREAST MILK

CROSS-REFERENCE

The present application is a non-provisional of, and claims the benefit of, U.S. Provisional Patent Application 62/429,657, filed on Dec. 2, 2016, and is a continuation of U.S. patent application Ser. No. 15/829,779, filed Dec. 1, 2017, the entire contents of each of which are incorporated herein by reference.

This application is related to the following patent applications: U.S. application Ser. No. 14/221,113; U.S. application Ser. No. 14/616,557; U.S. application Ser. No. 14/793,606; U.S. application Ser. No. 14/793,613; U.S. application Ser. No. 14/858,924; U.S. application Ser. No. 15/094,704; U.S. application Ser. No. 15/349,917; U.S. application Ser. No. 15/581,973; and PCT Application No. PCT/US2017/049961, the disclosures of which are incorporated herein by reference in their entirety.

BACKGROUND OF THE INVENTION

Breast pumps are commonly used to collect breast milk in order to allow mothers to continue breastfeeding while apart from their children. Currently, there are two primary types of breast pumps: manually-actuated devices, which are small, but inefficient and tiring to use, and electrically-powered devices, which are efficient, but large and bulky. Many existing breast pumps are pneumatic systems, wherein a tube is attached to a drive system to transmit vacuum from the drive system to a breast fluidly sealed against a breast interface.

It would be desirable to provide improved breast pumps that are small, highly efficient, quiet, and comfortable. Additional features such as pump communication with personal computing or mobile devices, automatic milk production quantification and/or milk characterization, and automatic inventory tracking would be further desirable for enhanced user convenience. At least some of these objectives will be satisfied by the devices, systems, and methods disclosed below.

SUMMARY OF THE INVENTION

The present invention generally relates to medical devices and methods, and more particularly relates to devices and methods for expression and collection of human breast milk.

Disclosed herein are improved devices, systems, and methods for the expression and collection of breast milk, such as human breast milk. In particular, described herein are pumping devices and systems suitable for use as hydraulic pumping systems, wherein vacuum is generated by the movement of liquids. Hydraulic pumping systems can have reduced pumping force requirements and hence reduced device size compared to pneumatic systems, while maintaining high pumping efficiency. Hydraulic breast milk expression systems can also be quieter and more comfortable for the user.

In one aspect, an apparatus for expression of breast milk from a breast comprises a breast shield assembly, the breast shield assembly comprising a breast interface and an actuatable assembly interface fluidly coupled with a tube. The breast interface is configured to engage the breast and the actuatable assembly interface is configured to removably couple to an actuatable assembly. The breast shield assembly comprises an enclosed fluid reservoir extending between the breast interface and the actuatable assembly interface, the fluid reservoir physically separated from the breast milk expressed from the breast and filled with a driving fluid comprising a liquid. The breast shield assembly comprises a fill port configured to allow addition or removal of the driving fluid to or from the fluid reservoir.

The fluid reservoir may comprise a first reservoir at the breast interface and a second reservoir at the actuatable assembly interface, the first reservoir and the second reservoir in fluid communication with one another via the tube.

The breast interface may comprise the fill port. The breast interface may be shaped to form a first opening to receive the breast therethrough, a second opening to couple to a collection container, a third opening to couple to the tube, and a fourth opening defining the fill port. The fill port may be positioned at a portion of the breast interface that protrudes maximally in any one direction. The actuatable assembly interface may comprise the fill port. The breast shield assembly may comprise two or more fill ports, wherein the breast interface may comprise at least one of the two or more fill ports, and the actuatable assembly interface may comprise at least one of the two or more fill ports.

The apparatus may further comprise a fill port plug configured to removably couple to the fill port so as to form a fluid-tight seal between the fill port plug and the fill port. The fill port plug may be tethered to the breast shield assembly. The fill port plug may comprise a flexible material. The fill port plug may comprise a cover portion and a plug portion, the cover portion configured to extend over the fill port along an outer surface of the breast interface or the actuatable assembly interface, and the plug portion configured to fit through the fill port, wherein the cover portion has an outer diameter that is greater than a diameter of the fill port. The plug portion may comprise an intermediate portion sized to fit snugly within the fill port and form a fluid-tight seal against an inner wall of the fill port, and an annular lip having an outer diameter that is greater than an outer diameter of the intermediate portion and greater than the diameter of the fill port. An inner surface of the plug portion may define a recessed central region surrounded by the annular lip, the recessed central region configured to allow the annular lip to flex radially outwards in response to inward pull forces exerted on the fill port plug.

The apparatus may further comprise an antimicrobial component in contact with the driving fluid, the antimicrobial component configured to reduce microbial growth in the driving fluid. The antimicrobial component may comprise a copper alloy, copper, brass, bronze, silver, an antimicrobial polymer, polymeric biocides, or a combination thereof. The antimicrobial component may be coupled to an inner surface of the tube.

In another aspect, a method of expressing breast milk from a breast comprises providing a breast shield assembly comprising a breast interface configured to engage the breast and an actuatable assembly configured to removably couple to an actuatable assembly, wherein the breast shield assembly comprises an enclosed fluid reservoir extending between the breast interface and the actuatable assembly interface. The method further comprises adding a liquid driving fluid to the fluid reservoir through a fill port of the breast shield assembly. The method further comprises engaging the breast with the breast interface, coupling the actuatable assembly interface to the actuatable assembly, and actuating the actuatable assembly to express the breast milk from the breast.

In another aspect, an apparatus for expression of breast milk from a breast comprises a breast interface configured to engage and fluidly seal against the breast, the breast interface comprising a housing and a membrane coupled to the housing to form a fluid reservoir therebetween, wherein the fluid reservoir filled with a driving fluid comprising a liquid. The breast interface comprises a coupling portion configured to couple to a collection container while fluidly isolating the collection container from the fluid reservoir. The coupling portion comprises one or more venting features configured to provide an air gap between the collection container and the coupling portion, thereby allowing an internal volume of the collection container to vent to atmospheric pressure.

The one or more venting features may comprise one or more protruding ribs protruding from a bottom surface of the coupling portion, the one or more protruding ribs configured to partially contact a top surface of the collection container when the collection container is coupled to the breast interface, thus providing one or more air gaps between the collection container and the coupling portion. The coupling portion may be further shaped to form an annular lip disposed closer to a center of the coupling portion than the one or more protruding ribs, the annular lip protruding past the one or more protruding ribs so as to reduce splashing of expressed breast milk towards the one or more air gaps.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4A shows an isometric view of an exemplary membrane suitable for incorporation with a breast interface;

FIG. 4B shows a front view of the membrane of FIG. 4A;

FIG. 4C shows a bottom view of the membrane of FIG. 4B;

FIG. 7A shows a top view of an exemplary coupling portion of a breast interface housing suitable for incorporation with a breast interface;

FIG. 7B shows a bottom view of the coupling portion of FIG. 7A;

FIG. 7C shows a sectional view of the coupling portion of FIG. 7A;

FIG. 7D shows a side cross-sectional view of the coupling portion of FIG. 7A;

DETAILED DESCRIPTION OF THE INVENTION

Specific embodiments of the disclosed systems, devices, and methods will now be described with reference to the drawings. Nothing in this detailed description is intended to imply that any particular component, feature, or step is essential to the invention. Although the present invention primarily relates to breast milk, any description herein of expression and collection of breast milk can also be applied to other types of fluids expressed from the breast, such as colostrum.

Disclosed herein are improved devices, systems, and methods for the expression and collection of breast milk, such as human breast milk. In particular, described herein are pumping devices and systems suitable for use as hydraulic pumping systems, wherein vacuum is generated by the movement of liquids. Hydraulic pumping systems can have reduced pumping force requirements and hence reduced device size compared to pneumatic systems, while maintaining high pumping efficiency. Hydraulic breast milk expression systems can also be quieter and more comfortable for the user. Some exemplary hydraulic pumping systems for breast milk expression are described in co-pending U.S. patent application Ser. Nos. 14/221,113, 14/616,557, 14/793,606, 14/793,613, and 15/349,917, and U.S. Provisional Patent Application Nos. 62/329,917 and 62/382,736, the entire disclosures of which are incorporated herein by reference.

Figure 1:
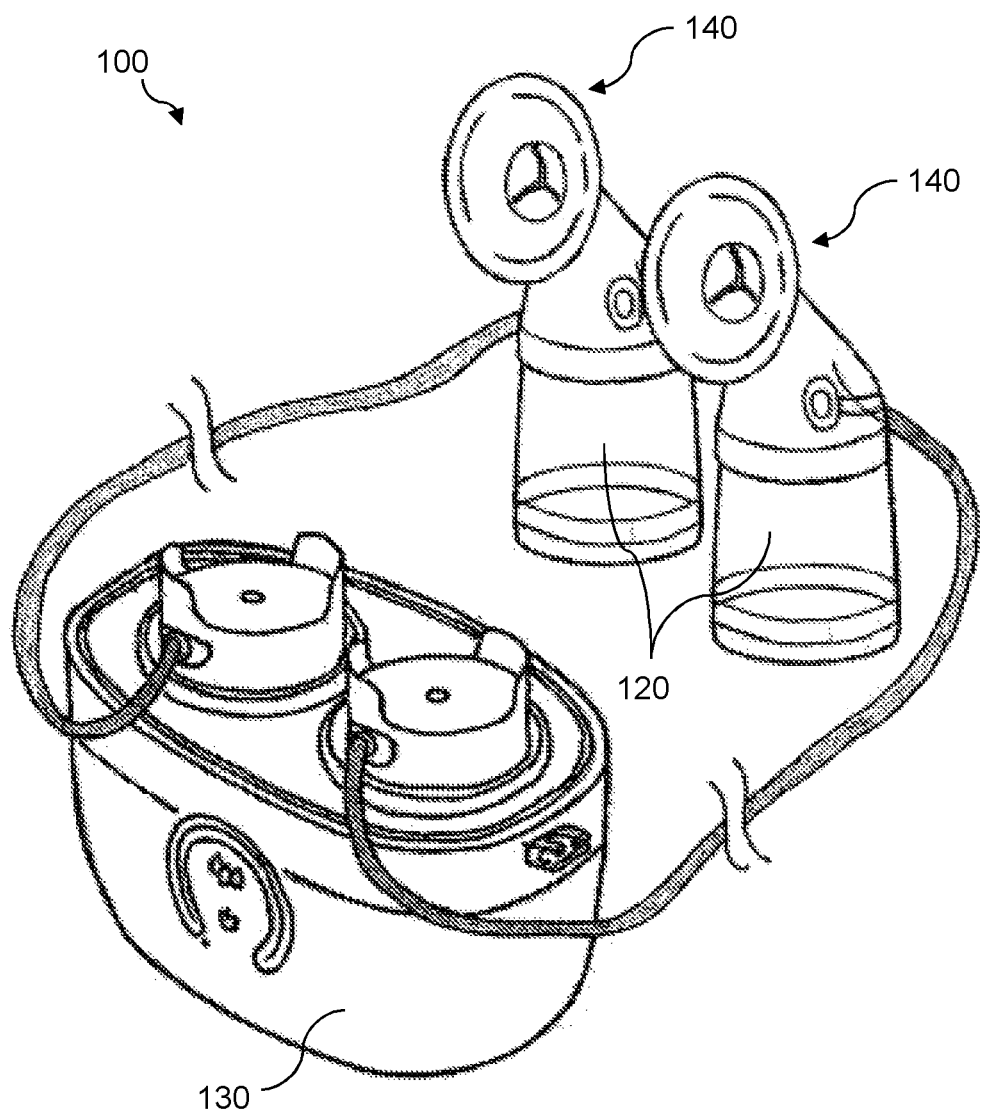
FIG. 1 illustrates an exemplary hydraulic breast milk expression system.

FIG. 1 illustrates an exemplary hydraulic breast milk expression system in accordance with embodiments. The system 100 comprises a breast milk expression or pumping device 110 and one or more collection containers 120. The expression device 110 comprises an actuatable assembly 130 operably coupled to a breast shield assembly (BSA) 140. Each breast shield assembly 140 may be removably couplable to the actuatable assembly 130, wherein the actuatable assembly is preferably configured to allow coupling to two breasts shield assemblies to the actuatable assembly. In use, the breast shield assembly 140 is placed over a breast so as to position at least a portion of the breast including the nipple within the breast shield assembly. The actuatable assembly 130 is subsequently actuated, such that the breast shield assembly becomes fluidly sealed against the breast, and cyclically applies negative pressure to the breast to cause expression of milk from the nipple.

Figure 2:
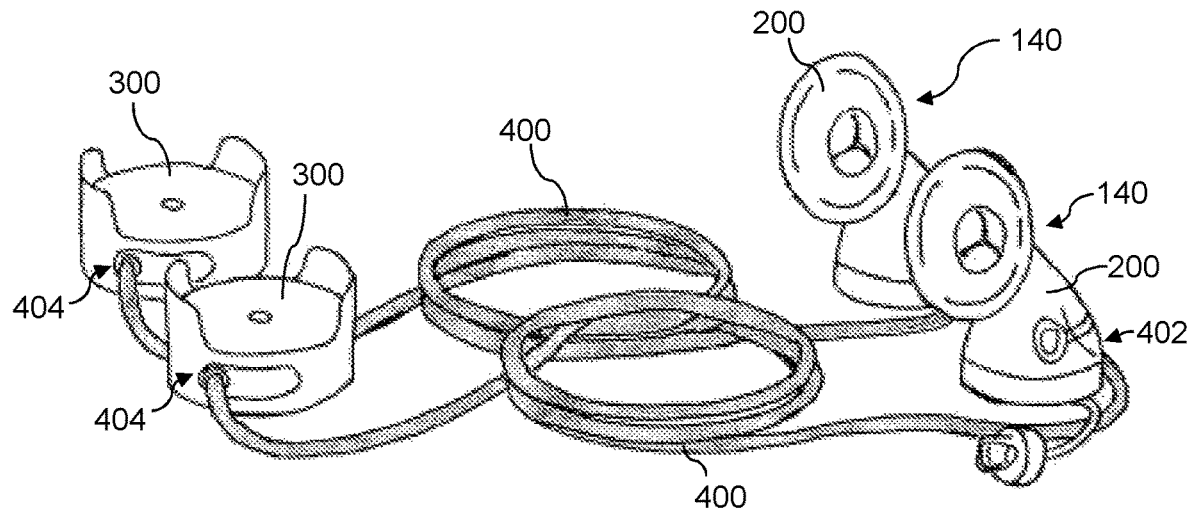
FIG. 2 illustrates exemplary breast shield assemblies suitable for incorporation with embodiments.

FIG. 2 illustrates exemplary breast shield assemblies suitable for incorporation with any breast milk expression system as described herein. A breast shield assembly 140 may be a part of the breast milk expression system 100 shown and described with reference to FIG. 1, for example. Each breast shield assembly 140 may comprise a breast shield or breast interface 200 coupled to an actuatable assembly interface (AAI) 300 via a tube 400. The breast interface 200 may be configured to engage the breast, while the AAI 300 may be configured to couple to the actuatable assembly. The tube 400 may comprise a first end 402 and a second end 404, wherein the tube may be coupled to the breast interface 200 at the first end and to the AAI 300 at the second end. The tube 400 operably couples the breast interface 200 with the AAI 300, such that when the actuatable assembly is actuated with the AAI 300 coupled thereto, pressure is transferred from the actuatable assembly to the AAI, then from the AAI to the breast interface 200 via the tube 400. As described in further detail herein, the breast interface may comprise an expandable membrane coupled to a rigid housing to form a fluid reservoir therebetween. The fluid reservoir may be filled with a driving fluid for the pump system, wherein the driving fluid may be any fluid such as air, a liquid, or a combination thereof. In many embodiments, the driving fluid may be a liquid such as water, or any other substantially incompressible fluid. The tube 400 may also be filled with the driving fluid and fluidly coupled to the reservoir. Actuation of the actuatable assembly can cause driving fluid to move within the tube and out of the fluid reservoir, causing the expandable membrane to expand and pull away from a breast sealingly engaged with the membrane, thereby generating negative pressure at the breast interface to cause expression of milk from the breast.

To begin a pumping session, the breast shield assembly may be operably coupled to the actuatable assembly via the actuatable assembly interface (AAI). The breast interface may then be placed over the nipple and the surrounding breast tissue, and the actuatable assembly actuated to initiate the pumping session. At the beginning of the pumping session, the fluid reservoir within the breast interface may be at atmospheric pressure ($P_{ATM}$). Throughout the pumping session, the actuatable assembly repeatedly alternates between an actuation phase and a resting phase. During the actuation phase, the driving fluid disposed within the tube moves towards the actuatable assembly, in turn causing the driving fluid disposed within the fluid reservoir to move out of the reservoir. The membrane accordingly expands and moves away from the breast tissue fluidly sealed against the membrane, causing the pressure at the breast interface to decrease to a pre-determined maximum negative pressure ($-P_{MAX}$) to cause expression of milk from the nipple. During the resting phase, the driving fluid within the tube moves away from the actuatable assembly and towards the breast interface, such that driving fluid moves back into the fluid reservoir. The membrane accordingly contracts and moves towards the breast, causing the pressure at the breast interface to increase from the maximum negative pressure $-P_{MAX}$ to either atmospheric pressure $P_{ATM}$ or a pre-determined minimum negative pressure ($-P_{MIN}$). The cyclical actuation of the actuatable assembly can thus mimic the sucking cycles of an infant during a nursing session. During each of the actuation phase and the resting phase, the fluid reservoir may be held at the maximum and minimum vacuum pressures, respectively, for a pre-determined length of time to model the nursing cycle of an infant.

Preferably, each breast shield assembly is a closed system, wherein the driving fluid remains contained within the breast shield assembly and physically separated from the expressed breast milk as well as from the actuatable assembly. Such a closed system can prevent cross-contamination between the expressed breast milk and the various components of the pumping device, and enable multiple users to share a single actuatable assembly, provided that each user has one or more breast shield assemblies of her own. Further, the easy separation of the breast shield assembly from the actuatable assembly can facilitate the storage and maintenance of the expression device.

Figure 3A:
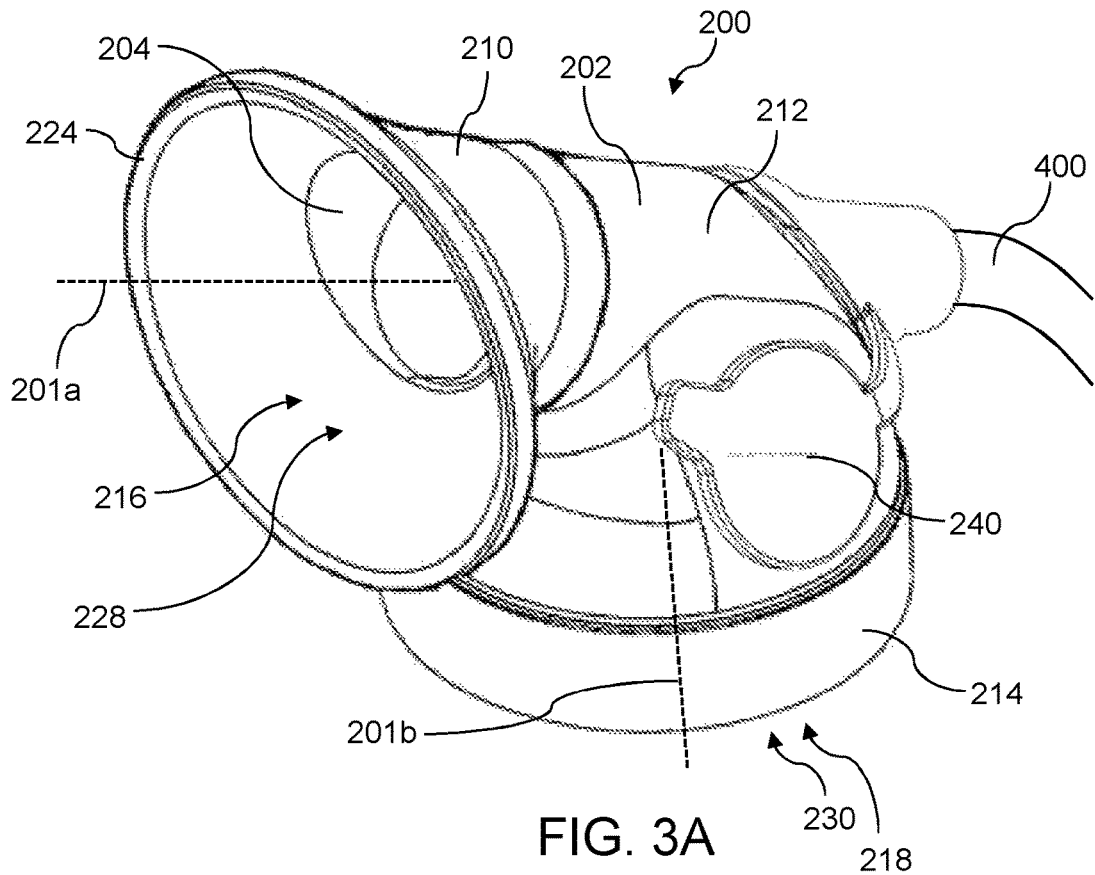
FIG. 3A shows an isometric view of an assembled breast interface suitable for incorporation with a breast shield assembly.
Figure 3B:
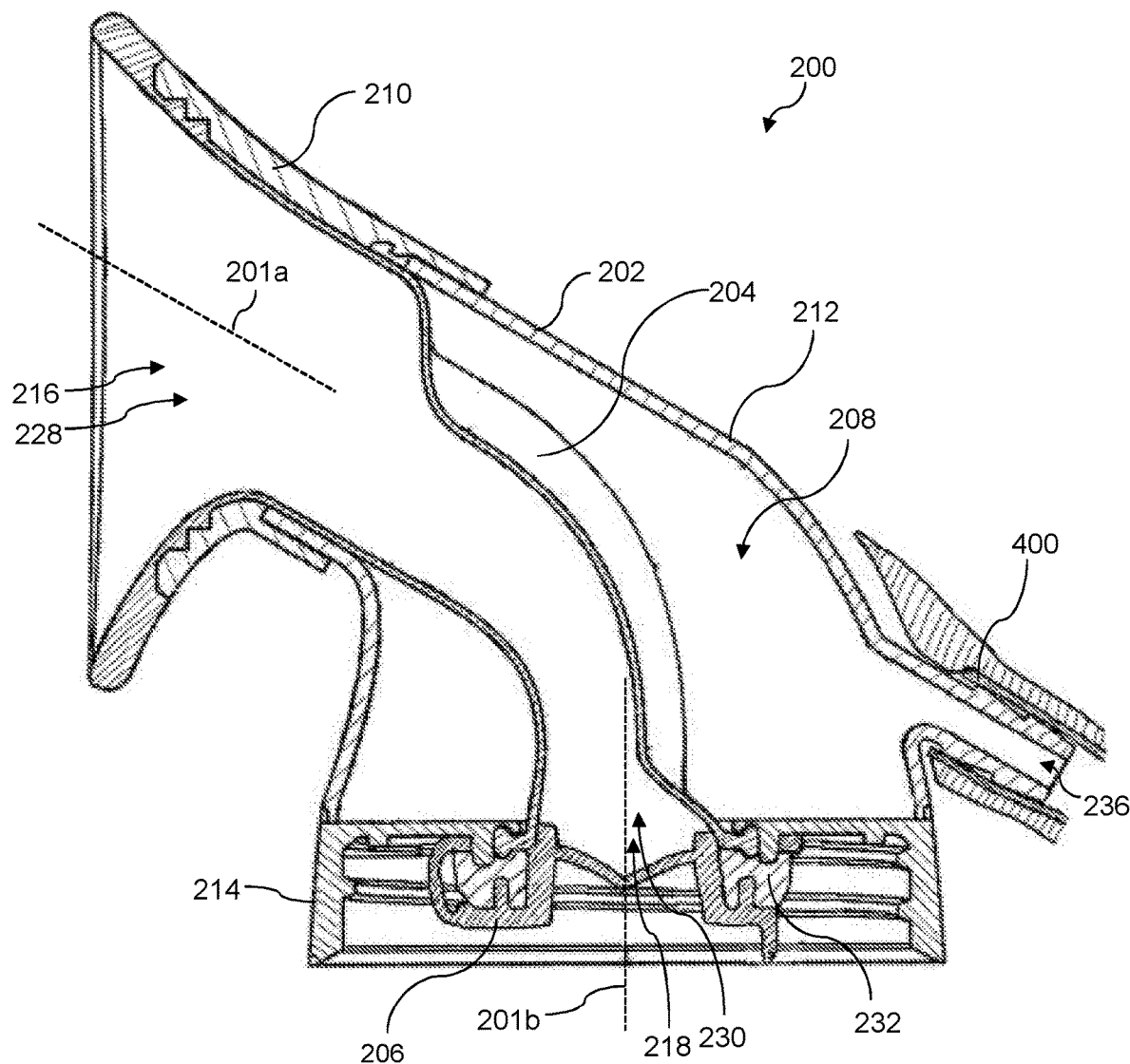
FIG. 3B shows a cross-sectional view of the assembled breast interface of FIG. 3A.
Figure 3C:
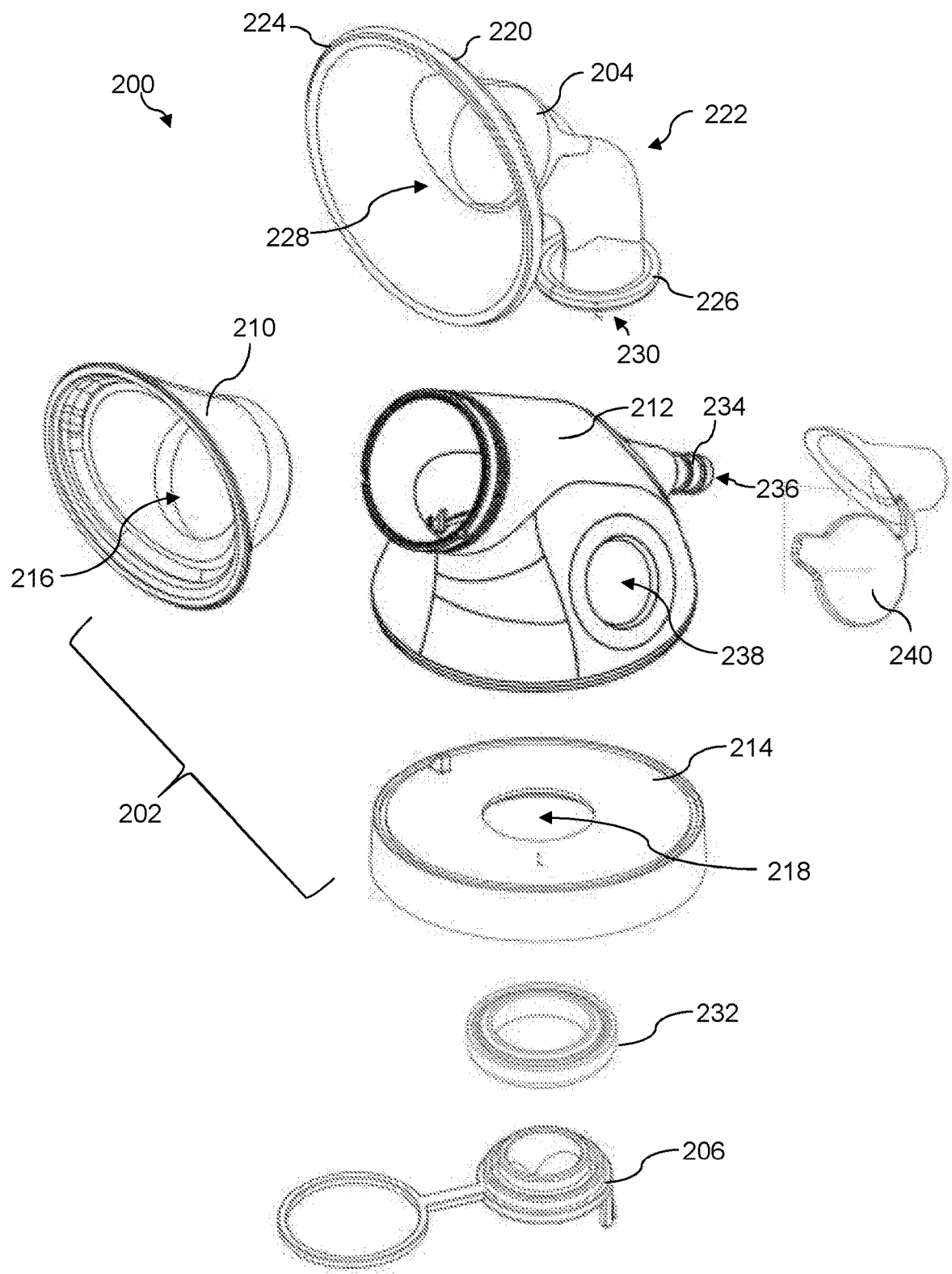
FIG. 3C shows an exploded view of the breast interface of FIG. 3A.

FIGS. 3A-3C illustrate an exemplary breast interface suitable for incorporation with any breast shield assembly as described herein. FIG. 3A is an isometric view of an assembled breast interface 200, FIG. 3B is a cross-sectional view of the assembled breast interface 200, and FIG. 3C is an exploded view of the breast interface 200. The breast interface 200 may comprise a housing 202, a membrane 204, and a valve 206. As best seen in FIG. 3B, the membrane 204 may be coupled to the housing 202 to form a fluid reservoir 208 therebetween, wherein the fluid reservoir may contain the driving fluid for the pumping system as described herein. The housing 202 may comprise a substantially rigid material to resist deformation in response to the negative pressure generated at the breast interface during actuation of the actuatable assembly. The membrane 204 may comprise an expandable portion 222 configured to deform in response to the negative pressure (e.g., constructed of a flexible material and/or comprising one or more expandable features such as pleats), so as to move away from or towards the breast. The valve 206 may be a one-way valve configured to allow drainage of the expressed breast milk therethrough during the resting phase of a pumping cycle (e.g., phase at which the breast interface is at atmospheric pressure, or other pre-determined minimum negative pressure for the system).

The housing 202 may comprise a flange portion 210, a body portion 212, and a coupling portion 214, wherein the three portions may be separate components that are coupled together as shown in FIGS. 3A-3C, or they may be portions of one or more continuous housing members. The flange portion 210 may form a first opening 216 of the housing configured to receive at least a portion of a breast therethrough. The coupling portion 214 may form a second opening 218 of the housing configured to allow drainage of the expressed breast milk therethrough. The coupling portion 214 may be configured to couple to a collection container as described herein in further detail herein. The body portion 212 may comprise a tube fitting 234 configured to interface with a tube 400 that operably couples the breast interface to the actuatable assembly, wherein the tube fitting forms a third opening 236 of the housing configured to allow driving fluid contained within the reservoir 208 to move into or out of the reservoir.

The membrane 204 may comprise a flange portion 220 and an expandable portion 222, wherein the flange portion may be configured to receive and fluidly seal against at least a portion of a breast, and the expandable portion may be configured to deform in response to actuation of the actuatable assembly to generate negative pressure at the breast interface. The flange portion and the expandable portion may be portions of a single, continuous membrane as shown in FIGS. 3B and 3C, or alternatively, the flange portion may be a separate component that is coupled to the membrane having the expandable portion. The membrane 204 may have a first end 224 adjacent the flange portion, and a second end 226 opposite the first end and adjacent the expandable portion. The first end may define a first opening 228 configured to receive the portion of the breast therethrough. The second end may define a second opening 230 configured allow drainage of the expressed breast milk therethrough into a collection container.

The membrane 204 may be coupled to the housing 202 with at least the expandable portion 222 disposed within the housing, to form the fluid reservoir 208 between the housing and the membrane. For example, as best shown in FIG. 3B, the first end 224 of the membrane may be coupled to the flange portion 210 of the housing to form a fluid-tight (airtight or watertight) seal therebetween, with the first opening 216 of the housing aligned with the first opening 228 of the membrane to define the first opening of the breast interface. The second end 226 of the membrane may be coupled to the coupling portion 214 of the housing to form a fluid-tight seal therebetween, with the second opening 218 of the housing aligned with the second opening 230 of the membrane to define the second opening of the breast interface. In preferred embodiments, the housing and the membrane are shaped such that the first and second openings of the housing and the membrane are rounded or substantially rounded, to facilitate the formation of a fluid-tight seal between the housing and the membrane at the first and second ends of the membrane. For example, as shown, the first and second openings of the housing and the membrane may be substantially circular in shape.

Collectively, the housing and the membrane may be configured such that, when in use with the user in a substantially upright position (e.g., standing or sitting), the first opening of the breast interface is directed substantially laterally to facilitate insertion of a breast through the first opening, and the second opening of the breast interface is directed substantially downwards to allow drainage of the expressed breast milk into the collection container. The breast interface may have a first central axis 201a extending through the first opening and a second central axis 201b extending through the second opening. The first central axis 201a may be oriented at a slight downward slope with respect to the horizontal plane, to ensure that expressed breast milk drains down towards the collection container. The second central axis 201b may extend substantially vertically, in alignment with a central longitudinal axis of the collection container coupled to the breast interface. The first central axis 201a may be oriented at an angle α with respect to the second central axis 201b, wherein the angle α may be within a range from about 95° to about 130°, or preferably about 110° to about 115°, to allow a user to express milk in a substantially upright position (e.g., sitting or standing) while maintaining proper milk drainage to the collection container.

Both the housing and the membrane may be configured to allow visualization of nipple placement within breast interface, to facilitate optimal placement of the breast interface over the breast. For example, the housing and the membrane may be constructed from materials that are optically clear or transparent, or sufficiently transluscent, such that the position of the nipple inserted into the breast interface is visible to the user. Alternatively, the housing and the membrane may comprise a portion that is transparent or transluscent to enable a user to see through said portion to visualize nipple placement within the breast interface.

Optionally, the breast interface 200 may further comprise a membrane retaining member 232 configured to secure the attachment of the membrane 204 to the housing 202. For example, as shown in FIGS. 3B and 3C, the membrane retaining member 232 may be a retainer ring configured to couple to the coupling portion 214 of the housing to capture or "sandwich" the second end 230 of the membrane between the coupling portion and the retaining member. In some embodiments, the membrane retaining member may be integrated with the housing, for example connected to the coupling portion 214 and configured to fold or snap over the second end 226 of the membrane to secure the membrane in place.

Optionally, the housing 202 may further define a fourth opening or a fluid fill port 238, and the breast interface 200 may be provided with a fill port plug 240 configured to close the fluid fill port. In some cases, it may be desirable to provide a user with the ability to easily drain or fill the breast shield assembly (the fluid reservoir 208 and the tube 400). For example, it may be necessary or desirable to drain the breast shield assembly during shipment or user travel, or it may be desirable to regularly replace the driving fluid in order to prevent development of microbial growth within the fluid. The fluid fill port can enable a user to easily fill or drain the breast shield assembly with the driving fluid, without requiring the user to disassemble the breast shield assembly (e.g., remove the tube 400 from the tube fitting 234 or the actuatable assembly interface). The fluid fill port 238 may be located on the body portion 218 of the housing as shown in FIGS. 3A and 3C, or it may be located at any other suitable portion of the housing that allows for substantially complete filling of the tube 400 and the reservoir 208.

Figure 4D:
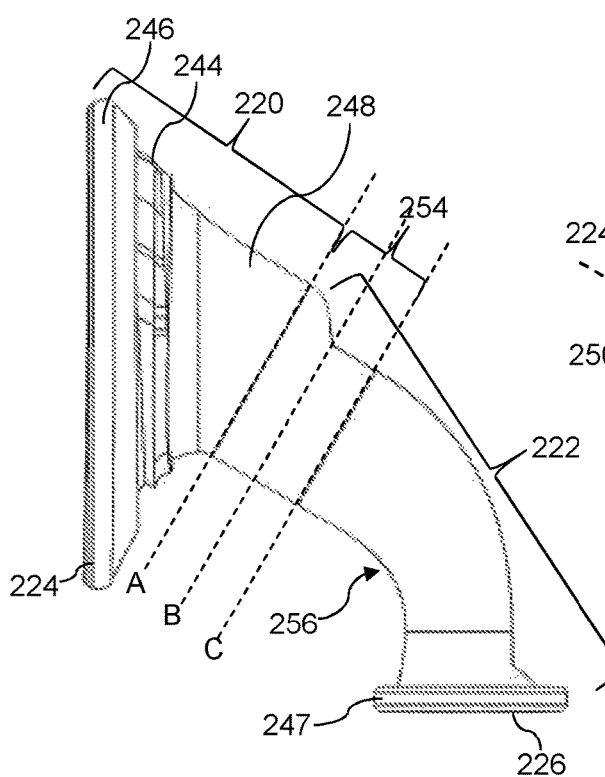
FIG. 4D shows a side view of the membrane of FIG. 4A.
Figure 4E:
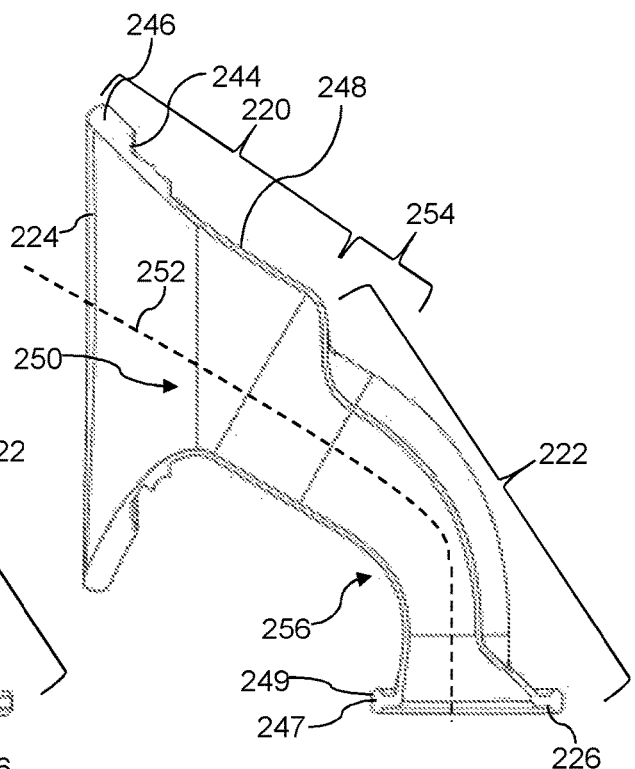
FIG. 4E shows a side cross-sectional view of the membrane of FIG. 4A.
Figure 4F:
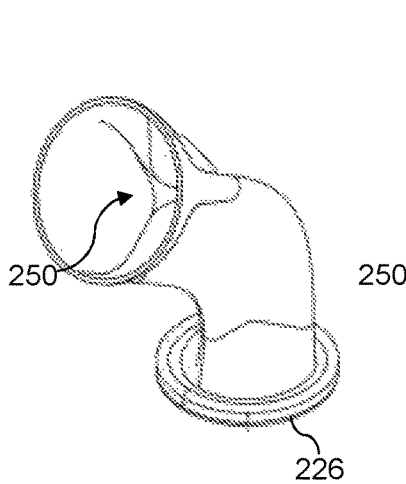
FIGS. 4F-4H show sectional views of the membrane of FIG. 4D along lines A, B, and C, respectively.
Figure 4G:
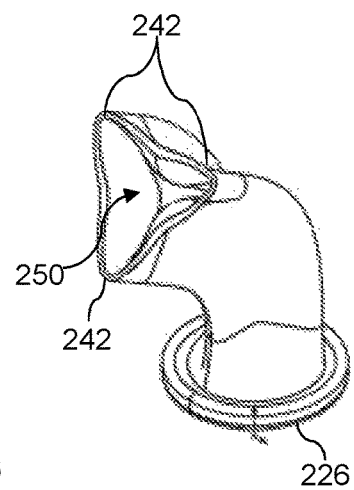
Figure 4H:
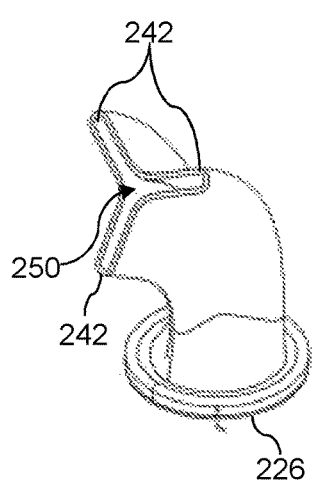

FIGS. 4A-4H illustrate an exemplary membrane suitable for incorporation with a breast interface as described herein. FIG. 4A is an isometric view, FIG. 4B is a front view, FIG. 4C is a bottom view, FIG. 4D is a side view, and FIG. 4E is a side cross-sectional view of membrane 204. FIGS. 4F-4H are sectional views of the membrane 204 of FIG. 4D along lines A, B, and C, respectively. The membrane 204 comprises the flange portion 220 and the expandable portion 222 as described herein, the flange portion adjacent the first end 224 of the membrane defining the first opening 228 configured to engage the breast, and the expandable portion adjacent the second end 226 of the membrane defining the second opening 230 configured to connect to a collection container. A central channel 250 may extend between the first opening and the second opening along the central axis 252 of the membrane (best seen in FIGS. 4D and 4E). The membrane may form a bend 256, at which point the central axis 252 of the membrane bends or changes orientation. Between the first end 224 of the membrane and the bend 256, the central axis 252 may be oriented at a slight downward slope with respect to the horizontal plane, such that the central channel adjacent the first opening can receive a breast therethrough with the user is in a substantially upright position, while ensuring that any expressed breast milk drains down along the membrane and into the collection container. Between the bend 256 and the second end 226 of the membrane, the central axis 252 may be oriented substantially vertically, to ensure that milk drains down into the collection container via gravity.

The flange portion 220 of the membrane 204 may comprise a first lip 246 adjacent the first end 224 of the membrane, configured to extend beyond the first end of the housing when the membrane is coupled to the housing (as best seen in FIG. 3B). Since the membrane 204 can comprise a material more flexible than the material of the housing, the first lip 246, consisting solely of the membrane material, can provide a soft, comfortable interface for the breast tissue sealed against the membrane. The flange portion may further comprise a sealing portion 248 configured to couple to and form a fluid-tight seal against the flange portion of the housing (as best seen in FIG. 3B). The thickness of the sealing portion 248 may be less than the thickness of the first lip 246, as best seen in FIG. 4E. The exterior surface of the sealing portion 248 may comprise one or more surface features such as grooves 244, configured to engage corresponding features of the housing flange portion to securely couple the membrane to the housing (see FIGS. 3B and 5A). The flange portion 220 may have a substantially frustoconical shape to accommodate the shape of the breast.

The membrane 204 may further comprise a second lip 247 adjacent the second end 226 of the membrane and extending beyond the expandable portion 222. The second lip 247 may be configured to engage and securely couple to a coupling portion of the housing. For example, the second lip 247 may comprise a protruding rim 249, configured to engage corresponding annular grooves of the coupling portion 214 and/or membrane retaining member 232 (see FIGS. 3B, 7C-7D, and 8).

The expandable portion 222 may comprise expandable features such as one or more pleats 242. For example, the membrane may comprise a plurality of radial pleats 242 distributed evenly about the circumference of the membrane. The pleats 242 may extend radially outward from the central axis 252 of the membrane, wherein the portions of the membrane between the pleats extend radially inwards towards the central axis of the membrane. When the actuatable assembly is actuated, the portions of the membrane between the pleats 242 can expand and contract radially and axially with respect to a nipple engaged within the membrane. The pleats may extend along substantially the complete length of the membrane between the flange portion 220 and the second end 226.

The expandable portion 222 may comprise a narrowing zone 254, wherein the portions of the membrane between the pleats increasingly extend inwards to progressively narrow the central channel 250. FIG. 4F shows a sectional view of the membrane 204 along line A as shown in FIG. 4D, at the beginning of the narrowing zone 254. Here, the central channel 250 still remains large enough to receive a nipple therethrough. FIG. 4G shows a sectional view of the member 204 along line B as shown in FIG. 4D, at a midpoint of the narrowing zone 254. At this point, the central channel 250 has begun to narrow, as the portions of the membrane between pleats 242 begin to extend radially inwards into the channel. FIG. 4H shows a sectional view of the member 204 along line C as shown in FIG. 4D, at the end of the narrowing zone 254. At this point, the central channel 250 has narrowed down to its minimum width, with the portions of the membrane between pleats 242 extending radially inwards into the channel to the maximum extent. The remainder of the expandable portion 222 between the narrowing zone 254 and the second end 226 may maintain a substantially similar cross-sectional geometry as at the end of the narrowing zone 254, as can be seen in FIG. 4C. At its minimum size or width as shown in FIG. 4H, the central channel 250 may be sufficiently small to prevent the nipple from fitting therethrough, but large enough to allow easy drainage of expressed breast milk therethrough. In use, a nipple may be received largely within the narrowing zone 254 with most of the surrounding breast tissue fluidly sealed against the flange portion 220. Such a configuration advantageously minimizes the amount of "dead space" within the breast interface through which the pump system must transfer the negative pressure to reach the breast tissue, thus improving the efficiency of pressure generation and transfer.

Figure 5A:
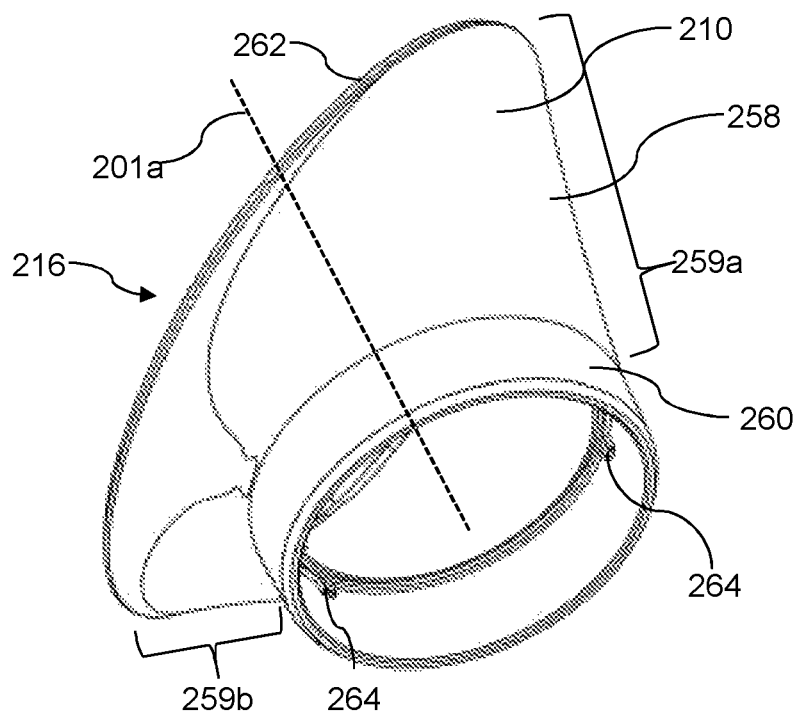
FIG. 5A illustrates an exemplary flange portion of a breast interface housing suitable for incorporation with a breast interface.

FIG. 5A illustrates an exemplary flange portion of a breast interface housing suitable for incorporation with any breast interface as described herein. The flange portion 210 comprises a substantially frustoconical portion 258 forming the first opening 216 of the housing and configured to engage the membrane flange portion as described herein. The flange portion 210 further comprises a sustantially cylindrical portion 260 configured to engage the body portion of the housing as described herein. The frustoconical portion 258 may comprise surface features such as grooves 262 configured to engage corresponding features of the flange portion of the membrane (as also seen in FIG. 3B). As described herein, the first central axis 201a of the breast interface at the first opening may be oriented in a slightly downward slope with respect to the horizontal plane to ensure proper milk drainage while the user pumps milk in an upright position. Accordingly, the frustoconical portion 258 may not be radially symmetric, wherein the depth 259a of the frustoconical portion at the top of the portion may be greater than the depth 259b at the bottom of the portion. To ensure proper alignment of a radially asymmetric flange portion with respect to the breast when the flange portion is coupled to the body portion of the housing, the cylindrical portion 260 may comprise one or more alignment features such as inner protrusions 264. The alignment features may be configured to engage corresponding alignment features of the housing body portion, as described herein, to ensure proper alignment of the two housing portions during assembly.

Figure 5B:
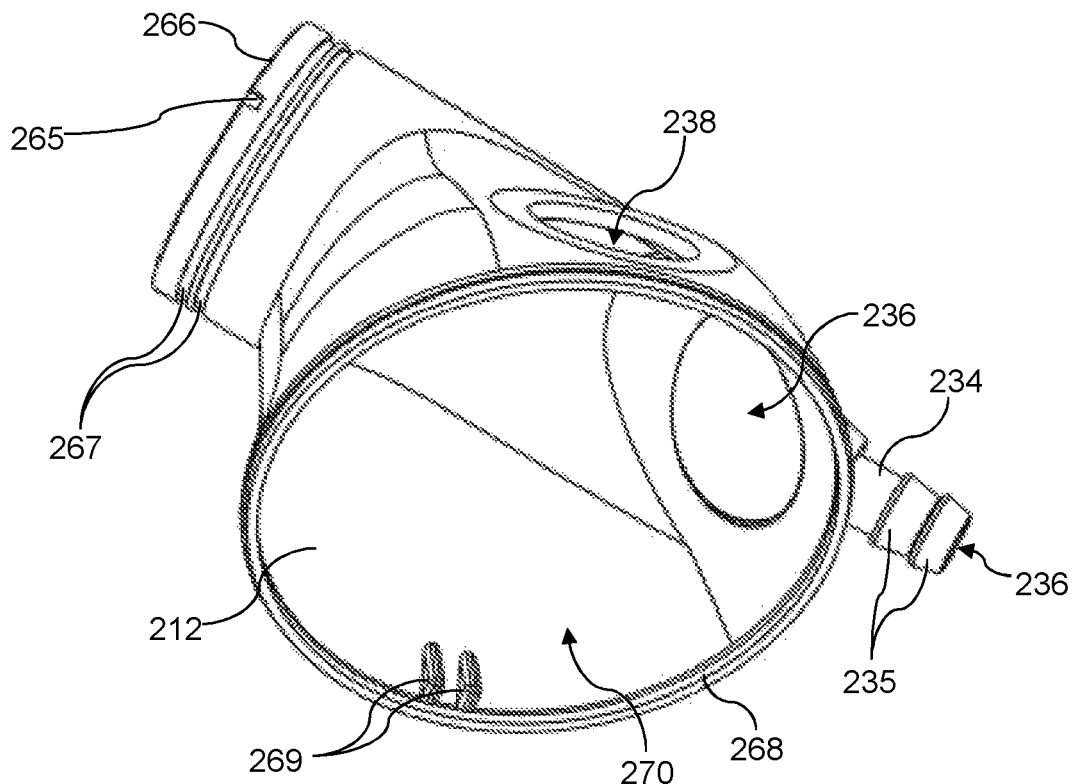
FIG. 5B illustrates an exemplary body portion of a breast interface housing suitable for incorporation with a breast interface.

FIG. 5B illustrates an exemplary body portion of a breast interface housing suitable for incorporation with any breast interface as described herein. The body portion 212 comprises a first end 266 configured to engage the cylindrical portion of the housing flange portion, and a second end 268 configured to engage the coupling portion of the housing as described herein. The first end 266 may comprise one or more alignment features such as indentations 265 on the outer surface, configured to engage corresponding alignment features of the housing flange portion such as inner protrusions 264 as shown in FIG. 5A. Optionally, the first end 266 may further comprise one or more features to ensure a fluid-tight seal between the flange portion and the body portion, such as one or more annular recessions 267 configured to receive o-rings therein.

The second end 268 of the body portion 212 may form an opening 270 that is greater than the second opening of the breast interface (as defined by second opening 218 of the coupling portion 214 and second opening 230 of the membrane 204, as shown in FIG. 3C). The difference between the size of the opening 270 and the second opening of the breast interface allows the fluid reservoir (208, FIG. 3B) to radially surround the membrane when the membrane is coupled to the housing, thus maximizing the efficiency of vacuum generation by the breast interface. The body portion 212 may comprise one or more alignment features adjacent the second end 268 configured to ensure proper alignment of the body portion 212 with the coupling portion. For example, as shown in FIG. 5B, the interior surface of the body portion may comprise a pair of protrusions 269 adjacent the second end, configured to capture therebetween a corresponding protrusion of the coupling portion.

As described herein, the body portion 212 may comprise a tube fitting 234 defining the third opening 236 of the housing. The tube fitting 234 may be configured to receive the tube (400, FIG. 2) of the breast shield assembly thereover, to fluidly couple the fluid reservoir (208, FIG. 3B) to the tube and thereby allow driving fluid contained within the reservoir to move into or out of the reservoir. The fitting may comprise one or more surface features such as barbs 235 to ensure a fluid-tight seal between the tube fitting and the tube.

Optionally, as described herein, the body portion may further define a fourth opening 238 of the housing, configured to function as a fluid fill port for the breast shield assembly. In preferred embodiments, the fill port 238 has a rounded or substantially circular shape, to facilitate the formation of a fluid-tight seal between the fill port and a fill port plug as described herein. The fill port 238 may be positioned at any portion of the housing that protrudes maximally in any one direction, such that the breast interface may be held with the fill port occupying the highest vertical position. Such a placement of the fill port can facilitate user filling of a breast shield assembly to the maximum possible extent.

Figure 6A:
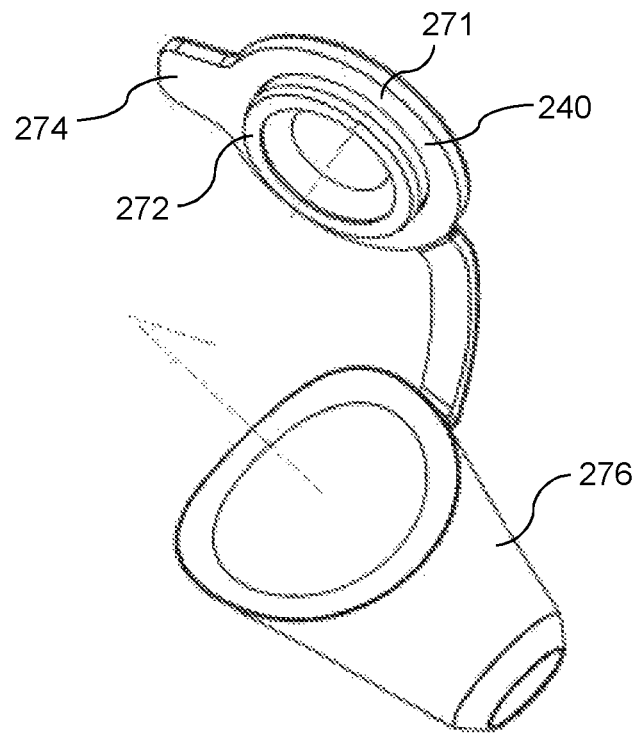
FIG. 6A illustrates an exemplary fill port plug suitable for incorporation with any breast interface.
Figure 6B:
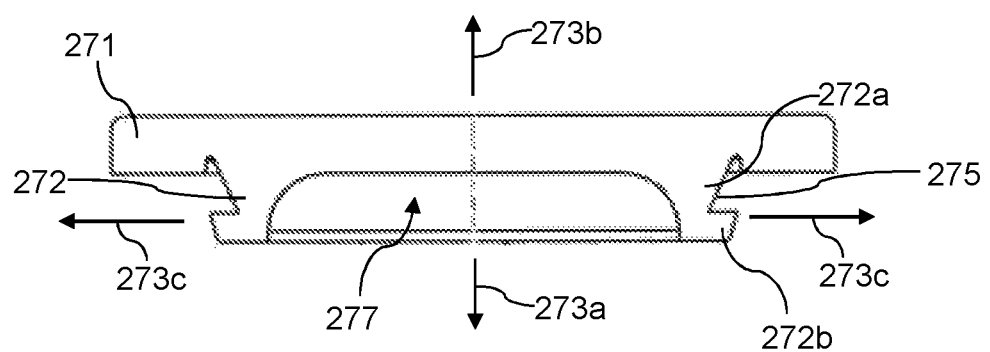
FIG. 6B shows a side cross-sectional view of the fill port plug of FIG. 6A.

FIG. 6A illustrates an exemplary fill port plug suitable for incorporation with any breast interface as described herein. The fill port plug 240 may comprise a flexible material, and may be shaped and sized to fit snugly within the fluid fill port of the housing to form a fluid-tight seal between the plug and the port. FIG. 6B is a side cross-sectional view of the fill port plug 240 of FIG. 6A. The fill port plug 240 may comprise a cover portion 271 and a plug portion 272. The cover portion 271 can be configured to extend over the fill port along the outer surface of the housing when the plug is coupled to the fill port. The cover portion 271 may have an outer diameter substantially greater than the diameter of the fill port, so as to resist inward pull forces 273a that may be experienced by the fill port plug while the plug is coupled to the fill port. The outer portion may comprise a pull tab 274 to facilitate user opening and closing of the fill port with the fill port plug. The plug portion 272 may be configured to fit through the fill port and form a fluid-tight seal against the inner wall of the fill port. The plug portion may comprise an intermediate portion 272a and an annular lip 272b. The intermediate portion 272a may have an outer diameter that is similar to or slightly greater than the inner diameter of the fill port to fit snugly within the fill port and form a fluid-tight seal thereagainst. The annular lip 272b may have an outer diameter that is greater than the outer diameter of the intermediate portion 272a, and substantially greater than the inner diameter of the fill port, so as to resist outer pull forces 273b that may be experienced by the fill port plug while the plug is coupled to the fill port.

The plug portion 272 may be a solid plug, or, as shown in FIGS. 6A and 6B, it may comprise an annular rim defining a recessed central region 277 along the inner (reservoir-facing) surface of the plug. When the breast interface is under negative pressure with the fill port plug coupled to the fill port, an inward pull force 273a may be applied to the fill port plug. The annular rim-shaped plug portion 272 may help protect the integrity of the fluid-tight seal between the plug and the fill port while the plug experiences such inward pull forces. In response to the forces 273a, the annular rim-shaped plug portion 272 can flex radially outwards in the direction shown by arrows 273c. Such flexing of the plug portion can compress the outer wall of the intermediate portion 272a against the inner wall of the fill port, further securing the fluid-tight seal between the plug and the fill port. Optionally, the intermediate portion 272a may be provided with a beveled outer wall surface 275, which may be beveled to have a greater outer diameter adjacent the cover portion than adjacent the annular lip 272b. The beveled surface 275 may help improve the fit of the intermediate portion 272a against the inner wall of the fill port, when the annular rim-shaped plug portion flexes in the direction 273c in response to the generation of vacuum pressure within the fluid reservoir.

Optionally, as shown in FIG. 6A, the fill port plug 240 may be tethered to a tube fitting cover 276, configured to be placed over a tube coupled to the tube fitting of the housing. The tube fitting cover can further secure the coupling between the tube and the tube fitting. When tethered to the tube fitting cover, which is coupled to the housing, the fill port plug may remain tethered to the breast shield assembly, so as to reduce the risk of misplacing the plug when the plug is removed from the port.

FIGS. 7A-7D illustrate an exemplary coupling portion of a breast interface housing, suitable for incorporation with any breast interface as described herein. FIG. 7A is a top view, FIG. 7B is a bottom view, FIG. 7C is a sectional view, and FIG. 7D is a side cross-sectional view of a coupling portion 214. As described herein, the coupling portion 214 may be configured to couple to the body portion of the housing and the second end of the membrane. The coupling portion may comprise a top 278 and a side wall 280. The top 278 may define the second opening 218 of the housing through which expressed milk may exit the breast interface to enter the collection container. The top 278 provides a physical barrier between the collection container and the fluid reservoir of the breast interface to fluidly isolate the collection container from the fluid reservoir, so as to prevent any mixing of the driving fluid with the expressed breast milk. The top 278 has a top surface 281 and a bottom surface 282, wherein the top surface 278 may be configured to engage the housing body and the membrane, and interface with the driving fluid contained within the fluid reservoir of the breast interface. The top 278 may further comprise one or more alignment features configured to facilitate the proper alignment of the coupling portion with respect to the housing body portion. For example, the top surface 281 may comprise a protrusion 279 configured to engage a corresponding pair of internal protrusions (269, FIG. 5B) of the housing body portion.

As best seen in FIGS. 7C and 7D, the side wall 280 comprises one or more features to couple to a collection container, such as a plurality of threads 283 formed on an interior surface of the side wall. The bottom surface 282 of the top 278 may comprise one or more venting features for the collection container, configured to provide an air gap between the container and the housing to allow the internal volume of the container to vent to atmospheric pressure. For example, the bottom surface may form protruding ribs 284 disposed about the periphery of the bottom surface and configured to align with the top surface of a collection container when the container is coupled to the breast interface. A protruding rib may have a protrusion depth that varies along different locations about the periphery of the bottom surface, such that the ribs come only into partial contact with the top of the collection container coupled to the coupling portion, thus providing a vent at the interface between the container and the housing. For example, as best shown in FIG. 7C, the bottom surface 282 may form two protruding rib 284 each extending along half of the circumference of the bottom surface, wherein the protrusion depth of each rib gradually ramps down or decreases from one end to the other.

The bottom surface 282 may further define an annular groove 285 adjacent the opening 218, as best seen in FIGS. 7C and 7D. The annular groove 285 may be configured to receive a second lip of the membrane as described herein with reference to FIGS. 4A-4H. In particular, the annular groove may be shaped to mate with a protruding rim of the second lip of the membrane, to secure the coupling between the membrane and the housing. The bottom surface 282 may further define a protruding rim 286 configured to engage a corresponding annular groove of a membrane retaining member, as described herein.

Figure 8:
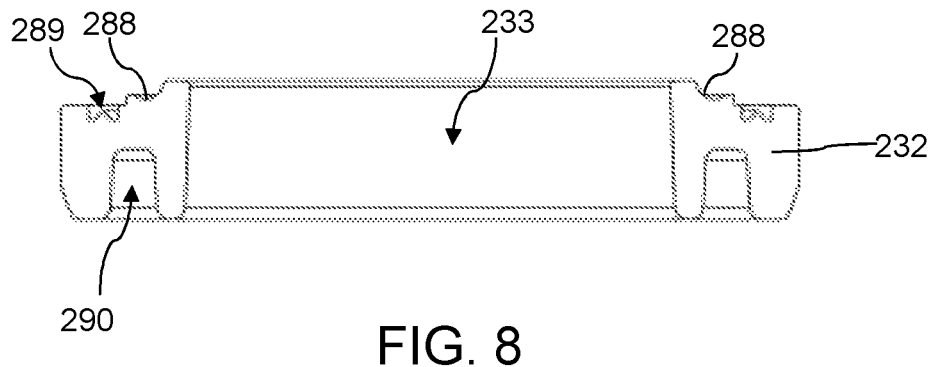
FIG. 8 shows a side cross-sectional view of an exemplary membrane retaining member suitable for incorporation with a breast interface.

FIG. 8 is a side cross-sectional view of an exemplary membrane retaining member suitable for incorporation with any breast interface as described herein. The membrane retaining member 232 can be a retaining ring as shown in FIGS. 3C and FIG. 8, wherein the retaining ring defines a central channel 233 configured to align with the second opening of the membrane when the ring is coupled to the breast interface. The top surface of the retaining ring may define a first annular groove 288, shaped to mate with and receive therein a protruding rim of the second lip of the membrane, as described herein with reference to FIGS. 4A-4H. In the assembled breast interface, the second lip of the membrane may be securely captured between the first annular groove 288 of the retaining ring and the annular groove 285 of the housing coupling portion (as best seen in FIG. 3B). The top surface of the retaining ring may further define a second annular groove 289, configured to receive the protruding rim (286, FIGS. 7C and 7D) of the coupling portion to securely couple thereto. The bottom surface of the retaining ring may define a third annular groove 290, configured to removably couple to a valve, as described herein.

Figure 9A:
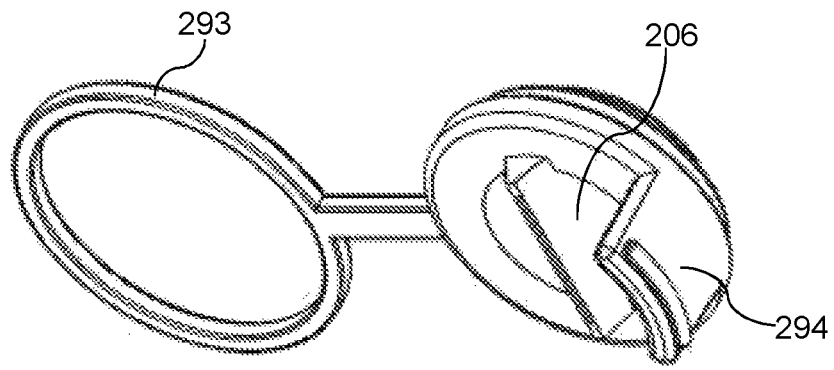
FIG. 9A illustrates an exemplary valve suitable for incorporation with a breast interface.
Figure 9B:
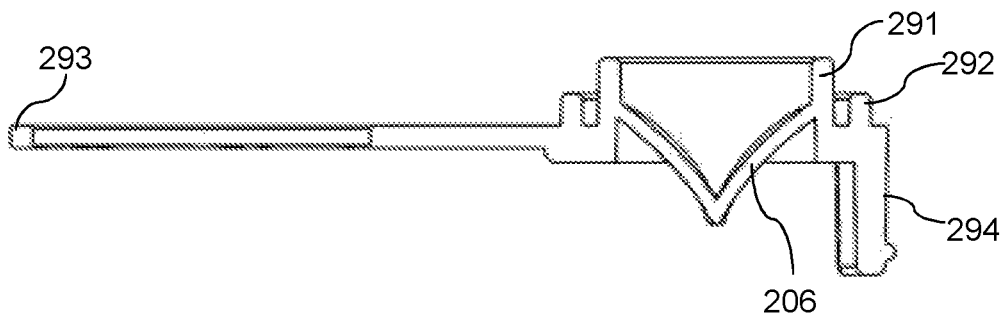
FIG. 9B shows a side cross-sectional view of the valve of FIG. 9A.

FIG. 9A illustrates an exemplary valve suitable for incorporation with any breast interface as described herein. FIG. 9B shows a side cross-sectional view of the valve of FIG. 9A. As described herein, the valve 206 may be a one-way valve configured to allow drainage of the expressed breast milk from the breast interface into the collection container, while preventing the backflow of milk or air from the collection container into the breast interface. For example, as shown in FIGS. 9A and 9B, the valve 206 may be duckbill valve. The valve may be configured to seal during the actuation phase of a pumping cycle, therefore maintaining the negative pressure generated at the breast interface during the actuation phase. During the resting phase of the pumping cycle, the valve may be configured to open to allow expressed breast milk to pass therethrough into the collection container.

As best seen in FIG. 9B, the valve 206 may comprise a first annular protrusion 291 and a second annular protrusion 292. The first annular protrusion 292 may be sized and shaped to fit snugly within the central channel of the membrane retaining member, and form a fluid-tight seal against the inner wall of the central channel. The second annular protrusion 292 may be sized and shaped to fit within the third annular groove (290, FIG. 8) of the membrane retaining member, to securely couple the valve to the breast interface. The valve 206 may be thus placed close to the second end of the membrane, so as to minimize the amount of dead space within the breast interface and thereby reduce pumping force requirements to achieve a target level of maximum negative pressure at the breast interface.

Optionally, the valve 206 may be configured to removably couple to the breast interface, in order to facilitate cleaning of the valve by a user. For example, the valve 206 may be constructucted at least partially of a flexible material, such that the first annular protrusion 291 of the valve 206 can be press fit into the third annular groove of the membrane retaining member in a removable fashion, without requiring substantial force to remove the valve. The valve may further comprise a pull tab 294 to facilitate user removal and replacement of the valve. Optionally, as shown in FIG. 9A, the valve 206 may be tethered to a retaining ring 293, configured to removably couple to the breast interface. For example, the retaining ring 293 may be sized and shaped to fit around the protruding rim 286 of the coupling portion 214 of the housing, wedged between the bottom surface 282 of the coupling portion and the top surface of the membrane retaining member (see FIGS. 3B and 7D). When tethered to the retaining ring 293, which is removably coupled to the housing, the valve may remain tethered to the breast interface, so as to reduce the risk of misplacing the valve T the valve is removed from the breast interface.

Figure 15A:
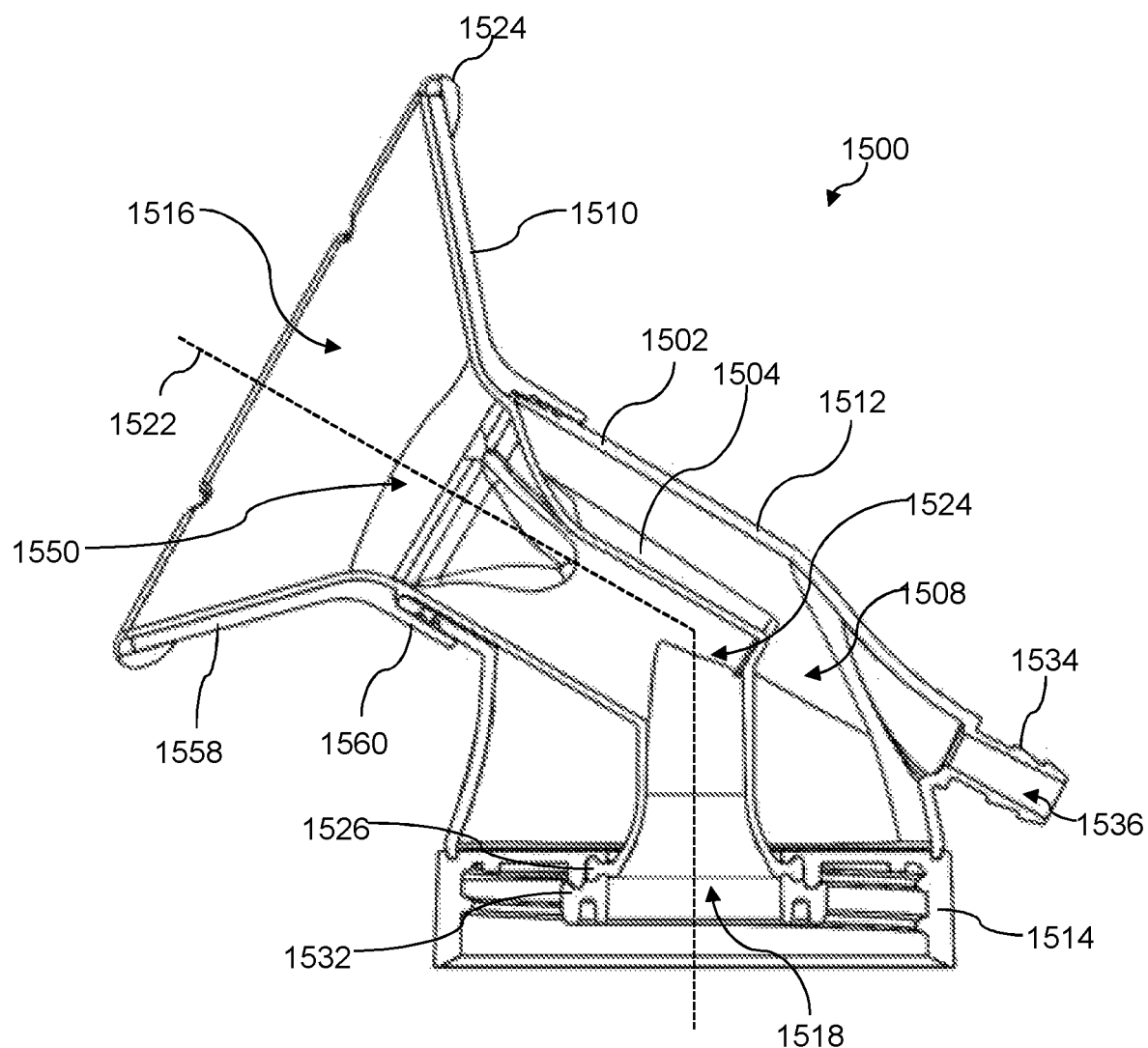
FIG. 15A is a side cross-sectional view of another exemplary breast interface.

FIG. 15A is a side cross-sectional view of an exemplary breast interface 1500, suitable for incorporation with any breast shield assembly as described herein. The breast interface 1500 may be similar in many aspects to breast interface 200 shown in and described with reference to FIGS. 3A-9B. The breast interface 1500 comprises a housing 1502 and a membrane 1504, coupled together to form a fluid reservoir 1508 therebetween, wherein each component may be similar in many aspects to similarly named components shown in and described with reference to FIGS. 3A-9B. For example, the housing 1502 may comprise a flange portion 1510, body portion 1512, and coupling portion 1514, wherein a membrane retaining member 1532 may be coupled to the coupling portion 1514 to securely capture the second end of the membrane 1504 therebetween. The housing may define a first opening 1516 configured to receive the nipple therethrough, a second opening 1518 configured to allow expressed breast milk to drain therethrough, a third opening 1536 shaped by a tube fitting 1534 and configured to allow driving fluid to enter and exit the fluid reservoir 1508, and optionally a fourth opening or a fill port (not shown) configured to allow a user to fill or drain the fluid reservoir with the driving fluid.

Figure 15B:
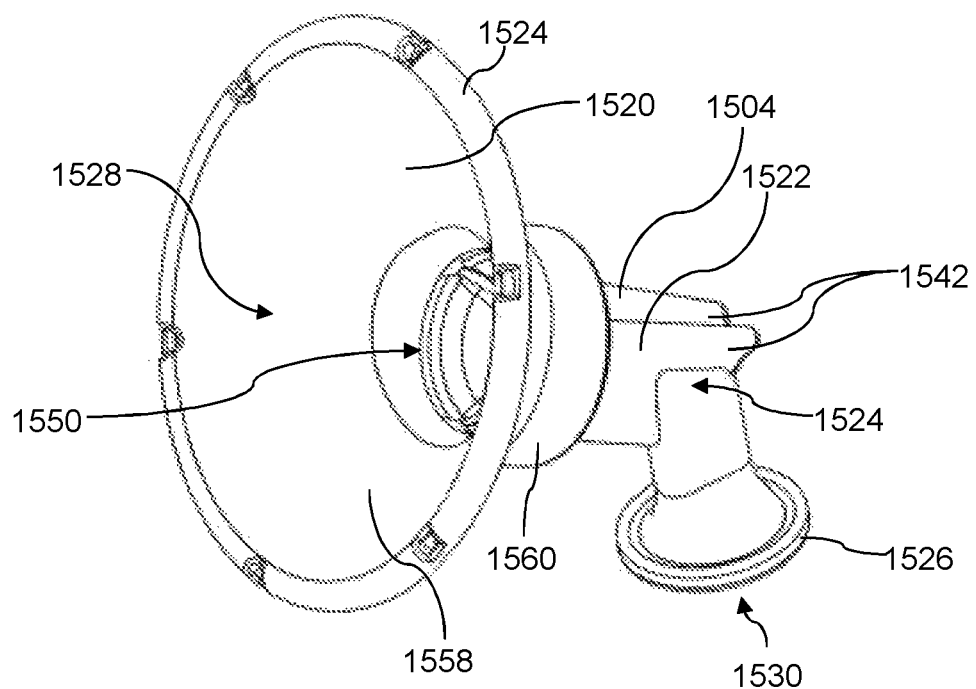
FIG. 15B is a side view of the flange portion and membrane of FIG. 15A, coupled together.
Figure 15C:
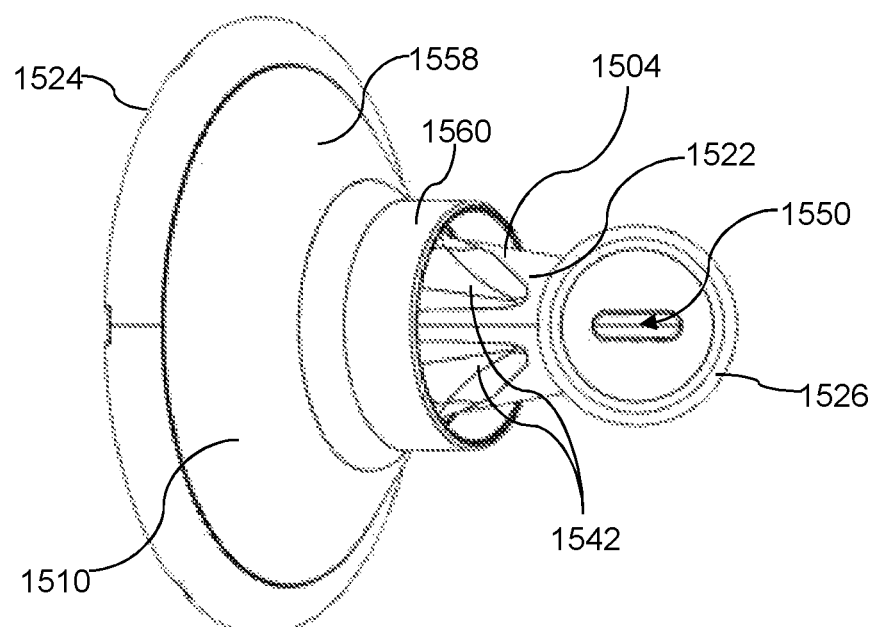
FIG. 15C is a bottom view of the flange portion and membrane of FIG. 15A, coupled together.

FIGS. 15B and 15C show the flange portion 1510 and membrane 1504 of FIG. 15A coupled together. FIG. 15B is a side view of the sub-assembly, and FIG. 15C is a bottom view. The flange portion 1510 may comprise a frustoconical portion 1558 and a cylindrical portion 1560, the frustoconical portion 1558 forming the first opening 1516 and configured to engage the breast tissue, and the cylindrical portion 1560 configured to engage the body portion 1512 of the housing. Unlike frustoconical portion 258 shown in FIGS. 3A-3C and 5A, frustoconical portion 1558 may be radially symmetric, having a radially uniform depth and angle with respect to the cylindrical portion. Other aspects of the flange portion 1510 may be similar to the flange portion 210.

The membrane 1504 may be similar in many aspects to membrane 204 shown in and described with reference to FIGS. 3A-4H. For example, membrane 1504 may comprise a first end 1524 shaped to form a first opening 1528 and a second end 1526 shaped to form a second opening 1530, wherein the first opening is configured to receive the nipple therethrough and the second opening is configured to allow expressed breast milk to exit the breast interface therethrough. A central channel 1550 may extend between the first and second openings along the central axis 1552 of the membrane (best seen in FIG. 15A). The membrane may form a bend 1524, at which point the central axis 1552 may change orientation; between the first end 1524 of the membrane and the bend 1556, the central axis 1552 may be orientated at a slight downward slope with respect to the horizontal plane, while between the bend 1556 and the second end 1526 of the membrane, the central axis may be oriented substantially vertically. The membrane may define a flange portion 1520 adjacent the first end and an expandable portion 1522 adjacent the second end. The flange portion 1520 may be coupled to the flange portion 1510 of the housing and configured to fluidly seal against breast tissue, and the expandable portion 1522 configured to expand and contract in response to movement of driving fluid into and out of the fluid reservoir of the breast interface. The expandable portion 1522 may comprise a plurality of expandable features such as radial pleats 1542 distributed evenly about the circumference of the membrane, wherein the pleats may extend increasingly inwards to progressively narrow the central channel 1550, as described with reference to membrane 204 of FIGS. 3A-4H. However, unlike in membrane 204, the pleats 1542 may extend along only a portion of the expandable portion 1522. For example, as shown, the pleats may extend only through the expandable portion disposed between the flange portion and the membrane bend 1524, and the portion between the bend 1524 and the second end 1526 of the membrane may be unpleated. The unpleated portion may still expand and contract in response to movement of the driving fluid in and out of the fluid reservoir, but to a lesser extent than the pleated portion. In order to minimize dead space and thereby maximize the efficiency of vacuum generation, the unpleated portion may be shaped to narrow the central channel 1550 down to a minimal width sufficient for allowing milk to pass therethrough.

Figure 16A:
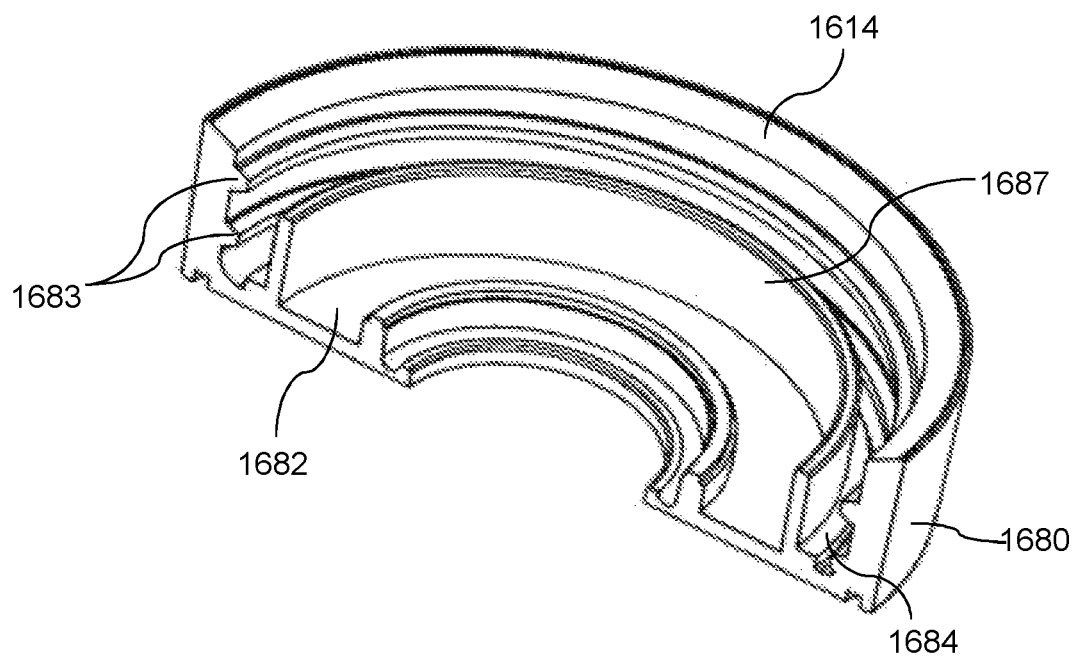
FIG. 16A is a sectional view of another exemplary coupling portion of a breast interface housing.
Figure 16B:
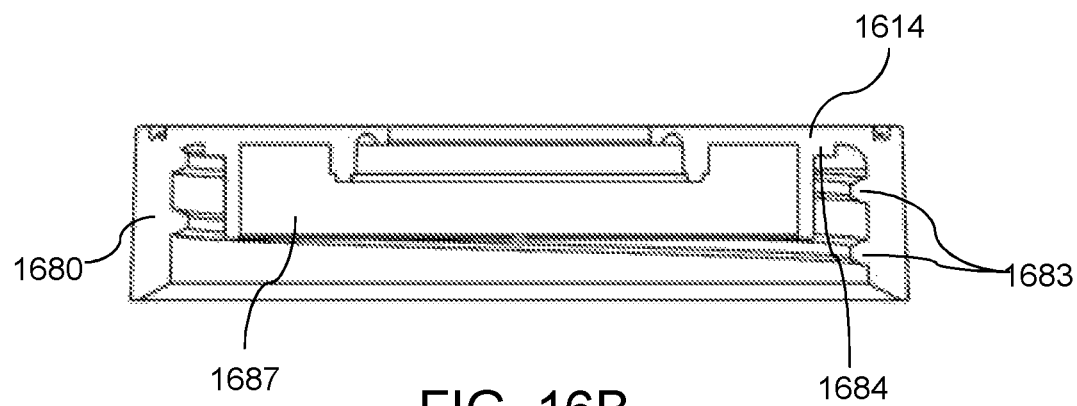
FIG. 16B is a side cross-sectional view of the exemplary coupling portion of FIG. 16A.

FIGS. 16A and 16B illustrate an exemplary coupling portion 1614 of a breast interface housing, suitable for incorporation with any breast interface as described herein. FIG. 16A is a sectional view, and FIG. 16B is a side cross-sectional view of the coupling portion 1614. The coupling portion 1614 may be similar in many aspects to coupling portion 214 shown in and described with reference to FIGS. 7A-7D. For example, coupling portion 1614 may comprise a side wall 1680 shaped to form a plurality of threads 1683, the threads configured to engage corresponding threads of a milk collection container. The coupling portion 1614 may further comprise a bottom surface 1682 defining one or more protruding ribs 1684 disposed about the periphery of the bottom surface and configured to align with the top surface of a milk collection container when the container is coupled to the breast interface. The protruding ribs can provide a vent at the interface between the container and the breast interface housing. Many features of the one or more protruding ribs 1684 may be similar to the those of the protruding ribs 184 described with reference to FIGS. 7A-7D. The coupling portion 1614 may further comprise an annular lip 1687 disposed closer to the center of the coupling portion than the protruding ribs 1684, the annular lip protruding past the ribs so as to prevent or reduce the splashing of expressed breast milk past the annular lip and towards the air gap between the container and the housing.

Figure 10A:
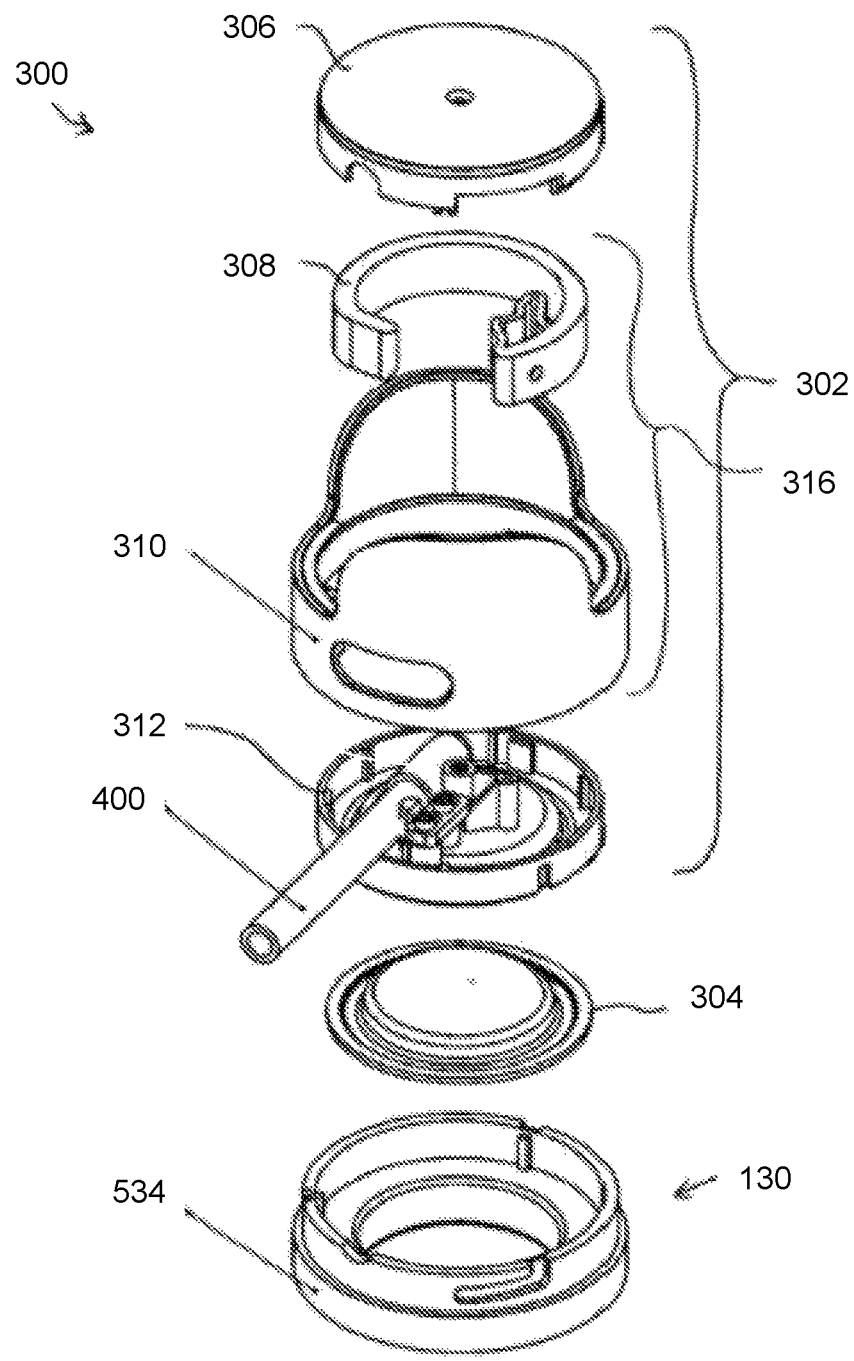
FIG. 10A shows an exploded view of an exemplary actuatable assembly interface (AAI) suitable for incorporation with a breast shield assembly.
Figure 10B:
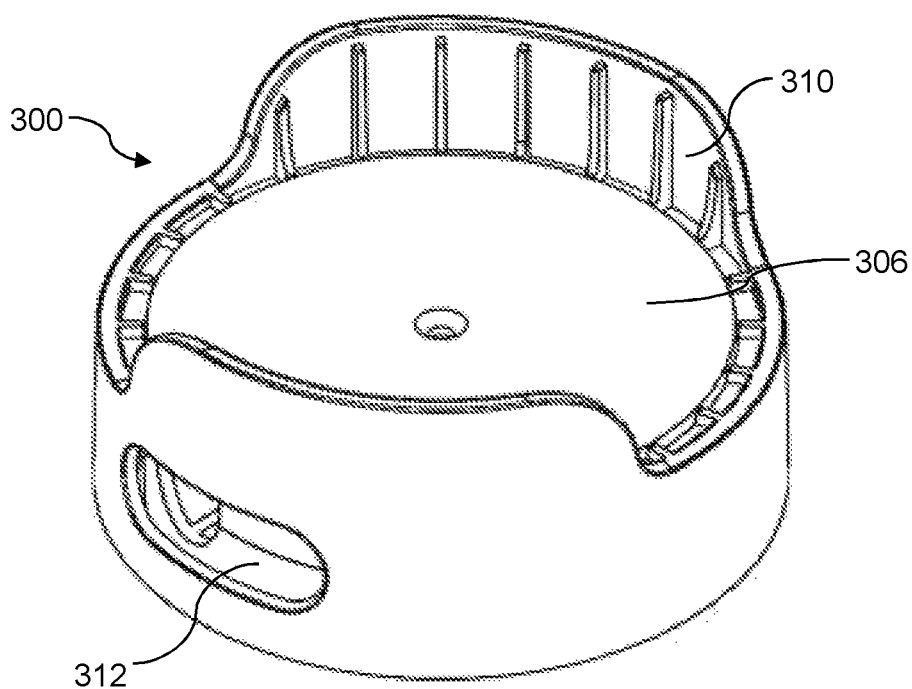
FIG. 10B shows an isometric view of the AAI of FIG. 10A.
Figure 10C:
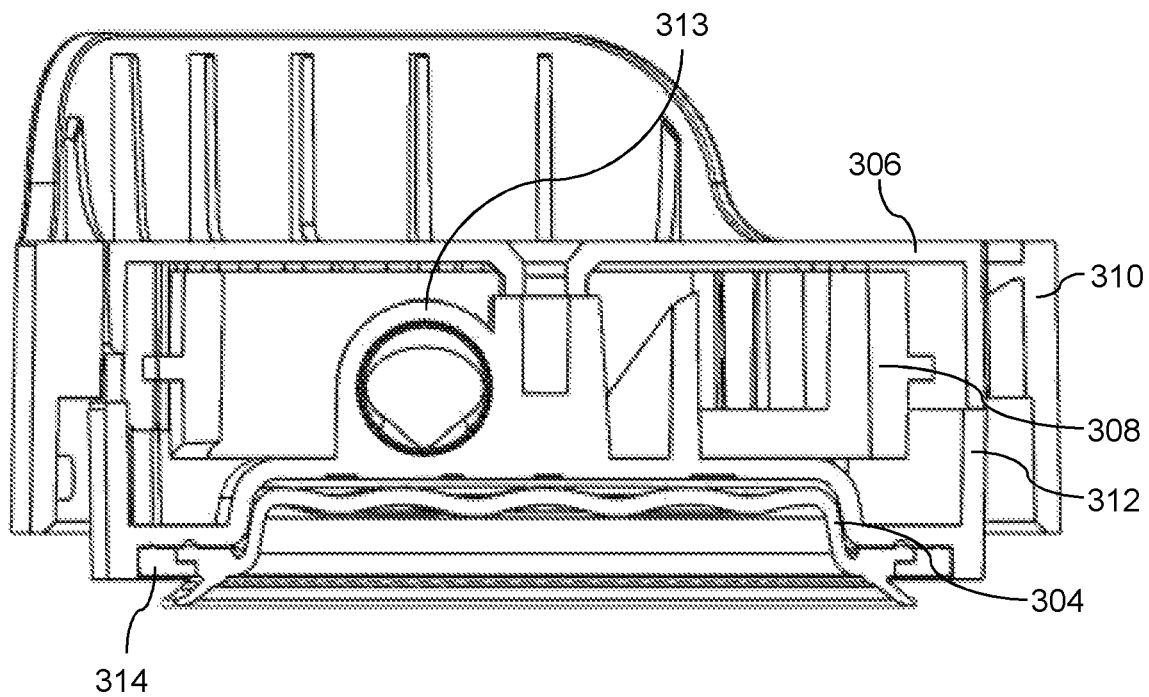
FIG. 10C shows a side cross-sectional view of the AAI of FIG. 10A.
Figure 10D:
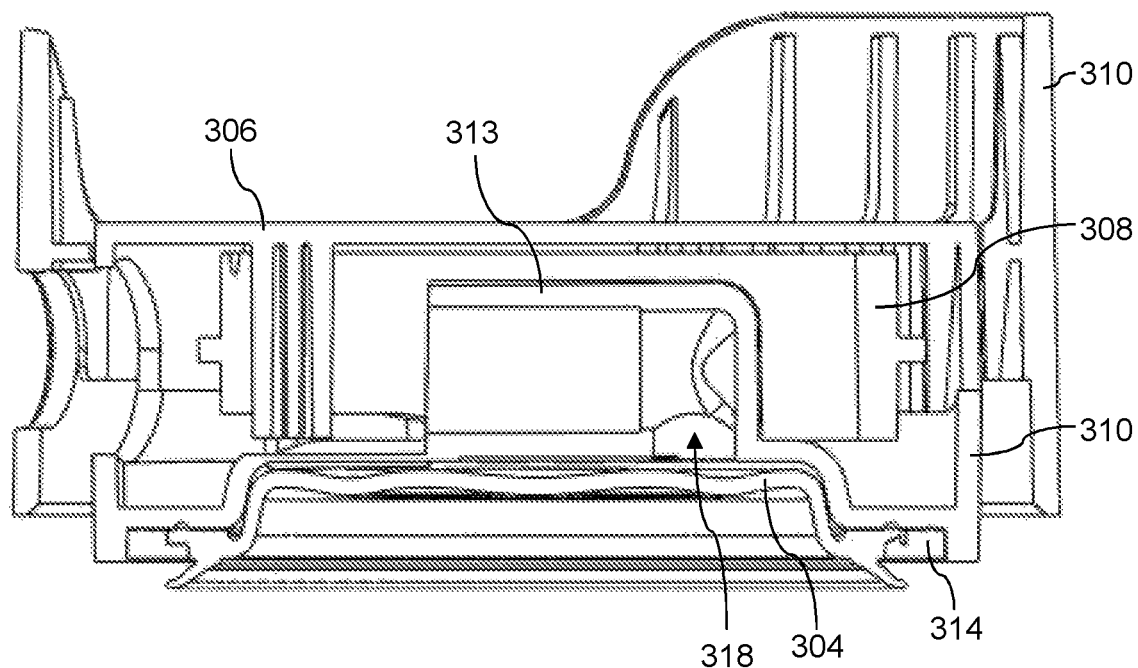
FIG. 10D shows a side cross-sectional view of the AAI of FIG. 10A.

FIGS. 10A-10D illustrate an exemplary actuatable assembly interface (AAI), suitable for incorporation with any breast shield assembly as described herein. FIG. 10A is an exploded view, FIG. 10B is an isometric view, and FIGS. 10C-10D are side cross-sectional views of the AAI 300. The AAI 300 can removably couple to the actuatable assembly of the breast milk expression device, so as to operably couple the actuatable assembly to the breast interface while keeping the mechanisms of the actuatable assembly physically separated from the driving fluid and the breast milk. The AAI 300 comprises an AAI housing 302 and a flexible AM membrane 304. The AAI membrane 304 is configured to operably couple to the driving mechanism in the actuatable assembly to move in response to actuation of the actuatable assembly, as described in further detail herein. The housing 302 comprises one or more components collectively configured to provide a locking mechanism for locking the AAI onto a corresponding locking portion 534 of the actuatable assembly 130. In the embodiment shown in FIGS. 10A-10D, the housing 302 comprises a cover 306, an internal locking ring 308, an external locking ring 310, and a base 312. The housing may further comprise a membrane-securing ring 314, as shown in FIGS. 10C and 10D. The AAI membrane 304 may be coupled to the bottom of the base 312, for example by being secured between the bottom surface of the base 312 and the membrane-securing ring 314. Tube 400, carrying the driving fluid for the pumping system and fluidly coupling the AAI to the breast interface, may be coupled to the AAI via the base 312, wherein the base may comprise a tube receiving member 313 configured to receive the tube 400 therein to form a fluid-tight seal thereagainst. The cover can be keyed and coupled to the base. The internal locking ring and external locking ring together form the locking ring assembly 316, which can rotate with respect to the locking portion 534 to lock the AAI onto the actuatable assembly.

The locking ring assembly can also rotate with respect to the base and the cover to provide a fluid communication shut-off mechanism, which shuts off fluid communication between the AAI and the breast interface when the breast shield assembly is disconnected from the actuatable assembly. For example, the locking ring assembly may comprise a mechanism to pinch off the tube 400 when the AAI is disconnected from the actuatable assembly, and release the tube from the pinching when the AAI is connected to the actuatable assembly. In contrast to air used to transfer pressure in penumatic pumping systems, a liquid driving fluid for a hydraulic system has a higher density than the atmosphere surrounding the driving fluid. As a result, when the breast shield assembly is disconnected from the actuatable assembly, positioning either the breast interface or the AAI above the other can apply head pressure to the membrane of the component positioned below the other, causing the membrane to distend or "bulge" outwards. For example, when the breast interface is positioned above the AAI, the AAI membrane can distend in a downward direction, making it difficult for a user to couple the AAI to the actuatable assembly. Shutting off the fluid communication between the breast interface and the AAI while the breast shield assembly is not connected to the actuatable assembly can decouple the breast interface membrane from the AAI membrane, thereby helping to ensure that both the breast interface membrane and the AAI membrane are in the proper configuration for beginning pumping.

As best seen in FIG. 10D, the base 312 and the AAI membrane 304 may be separated by a gap space 318, which may be in fluid communication with the tube 400 via the tube-receiving member 313 of the base. The gap space 318 may be filled with the driving fluid for the pump system. When the AAI is coupled to the actuatable assembly, actuation of the actuatable assembly can cause the AAI membrane 304 to move away from the base 312, increasing the volume of the gap space 318 such that driving fluid moves from the tube 400 into the gap space 318. This movement of the driving fluid in turn causes movement of the driving fluid out of the fluid reservoir at the breast interface, thereby generating negative pressure at the breast interface.

Additional details, features, and embodiments related to the fluid shut-off mechanism and the AAI may be found in U.S. Provisional Application Ser. No. 62/329,917, the entire disclosures of which are incorporated herein by reference.

Figure 11:
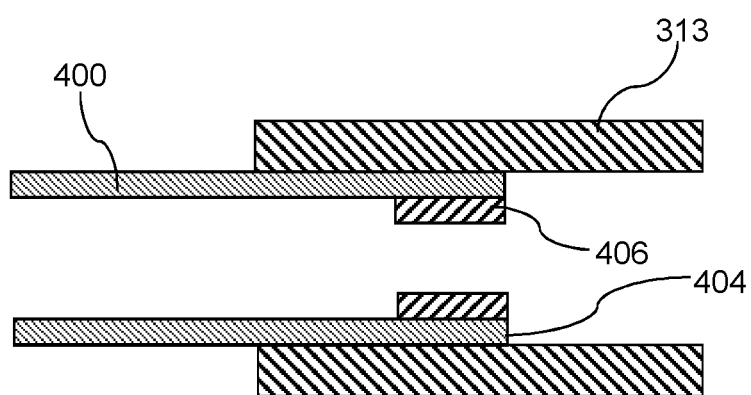
FIG. 11 schematically illustrates an exemplary embodiment of a tube suitable for incorporation with a breast shield assembly.

FIG. 11 schematically illustrates an exemplary embodiment of a tube 400, suitable for incorporation with any breast shield assembly as described herein. Optionally, the tube 400 may be provided with one or more antimicrobial components 406 in contact with the driving fluid, in order to reduce or prevent microbial growth in the driving fluid. For example, the inside of the tube may be lined with a small piece of copper or other material known to have antimicrobial properties (e.g., copper alloys such as brass and bronze, silver, antimicrobial polymers/polymeric biocides, etc). The antimicrobial component may be provided at any location of the breast shield assembly that comes in contact with the driving fluid, such as on an interior surface of the tube, an interior (reservoir-facing) surface of the housing, or an exterior (reservoir-facing) surface of the breast interface membrane. For example, referring to FIG. 11, a small piece of antimicrobial material 406 may be coupled to an inner surface of the tube 400 near the second end 404 of the tube configured to couple to the tube-receiving member 313 of the AM base. Alternatively or in combination with an antimicrobial material placed in contact with the driving fluid, the expression device may have an integrated microbicidal unit, such as a small ultraviolet LED assembly configured to irradiate the driving fluid with UV light. Such a UV assembly may be supported with the AAI or the actuatable assembly at any location that enables the light source to direct light into the driving fluid, and may draw power from the power source for the actuatable assembly, for example.

Figure 12A:
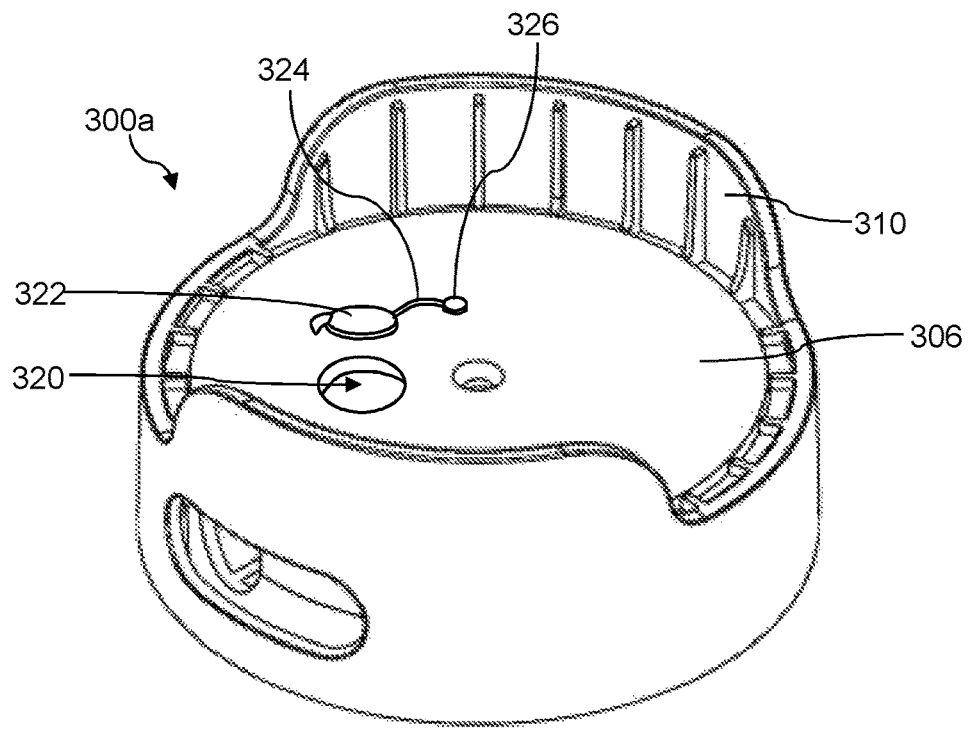
FIG. 12A shows an isometric view of an exemplary AAI suitable for incorporation with a breast shield assembly.
Figure 12B:
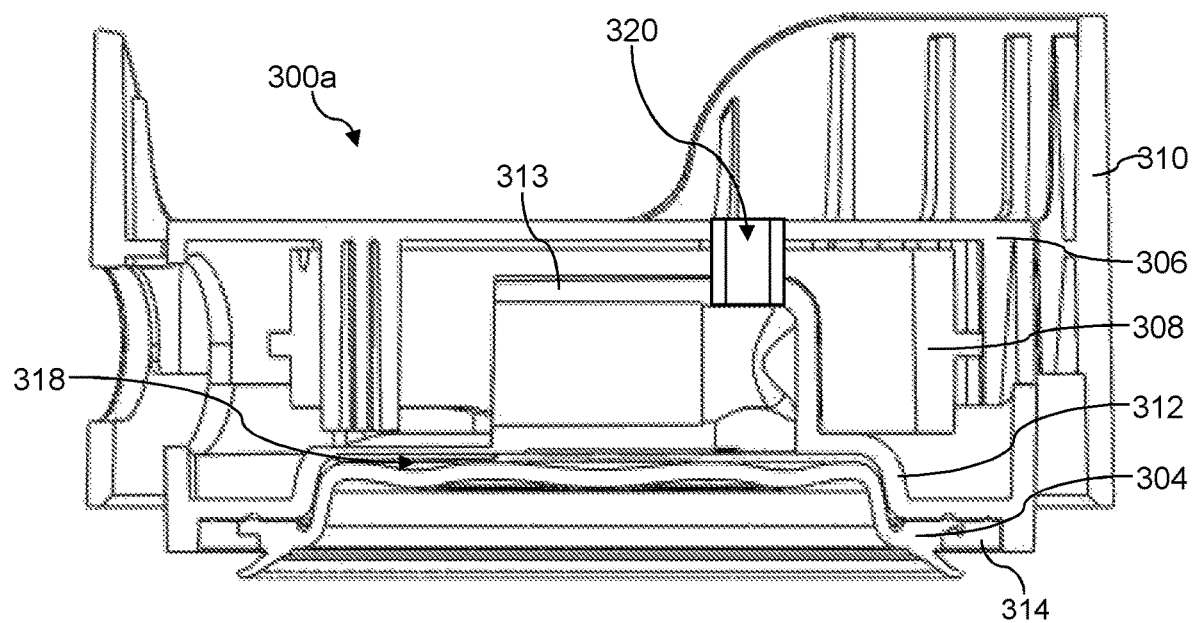
FIG. 12B shows a sectional view of the AAI of FIG. 12A.

FIGS. 12A and 12B illustrate an exemplary actuatable assembly interface (AAI), suitable for incorporation with any breast shield assembly as described herein. FIG. 12A is an isometric view, and FIG. 12B is a sectional view of the AAI 300a. AAI 300a may be substantially similar in many aspects to AAI 300 shown and described with reference to FIGS. 10A-10D, but may further comprise a fluid fill port 320 and a fill port plug 322. The fluid fill port 320 may be an optionally provided feature of any AAI as described herein, and may have a similar function as the fluid fill port of the breast interface shown and described with reference to FIGS. 3A-3C and FIG. 5B. The fluid fill port 320 of the AAI may provide a fluid inlet/out for the driving fluid, such that the breast shield assembly may be drained or filled with driving fluid. The fluid fill port 320 may extend from the AAI cover 306 through the AAI base 312, and may be positioned over the tube-receiving member 313 of the AAI base 312, so as to be in fluid communication with the tube of the breast shield assembly as well as the gap space 318 between the AAI membrane 304 and the base 312. To fill the breast shield assembly through the AAI fluid fill port 320, a user may hold the breast shield assembly with the AAI positioned at a higher plane than the breast interface, and add driving fluid through the port. The fill port plug 322 may be configured to removably couple to the fill port, and form a water-tight seal against the fill port when coupled thereto. To reduce the risk of misplacing the plug 322, the plug 322 may be provided with a tether 324 that couples to a peg 326 located on the AAI housing (e.g., the AAI cover 306), such that even when the plug is removed from the port, it remains attached to the AAI.

A breast shield assembly in accordance with embodiments may comprise a single fluid fill port located at the breast interface, a single fluid fill port located at the AAI, or both a fill port at the breast interface and another fill port at the AM.

Figure 13A:
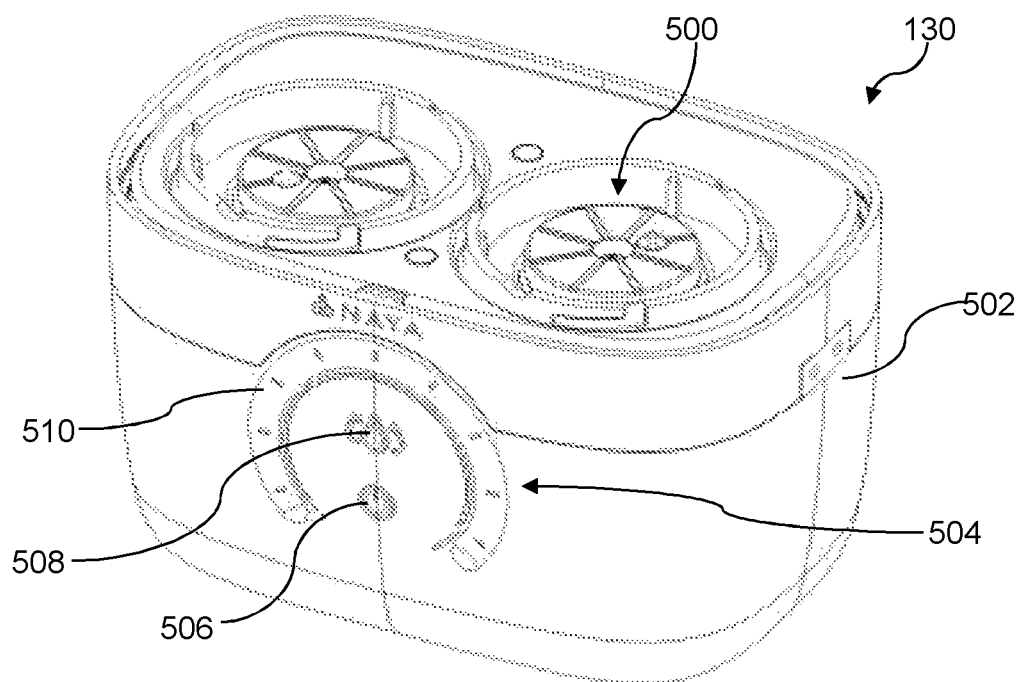
FIG. 13A illustrates an exemplary actuatable assembly suitable for incorporation with a breast milk expression device.

FIG. 13A illustrates an exemplary actuatable assembly suitable for incorporation with any breast milk expression device as described herein. The actuatable assembly 130 may comprise a driving mechanism 500 encased within a housing 502. The driving mechanism 500 may be configured to couple to and drive two breast shield assemblies, as shown. The housing 502 may be configured to protect the driving mechanism from physical stress, liquid egress, or other such potential source of damage to the mecanism. The housing 502 may provide a physical user interface 504 for controlling the operation of the driving mechanism. For example, as shown in FIG. 11A, the user interface 504 may comprise a power button 506 to start or stop actuation of the driving mechanism, a mode button 508 to toggle between different operational modes of the driving mechanism (e.g., a high-frequency cycle to stimulate milk let-down from the breast, and a lower-frequency cycle to efficiently express milk from the breast), and/or a power level selector 510 to select the vacuum level of a pumping cycle. The various buttons of the user interface 504 may be operably coupled to a processing unit disposed within the housing and configured to drive operation of the drive mechanism. The actuatable assembly 130 may be further configured to be controlled via a software user interface of a computing device, as described in further detail herein.

Figure 13B:
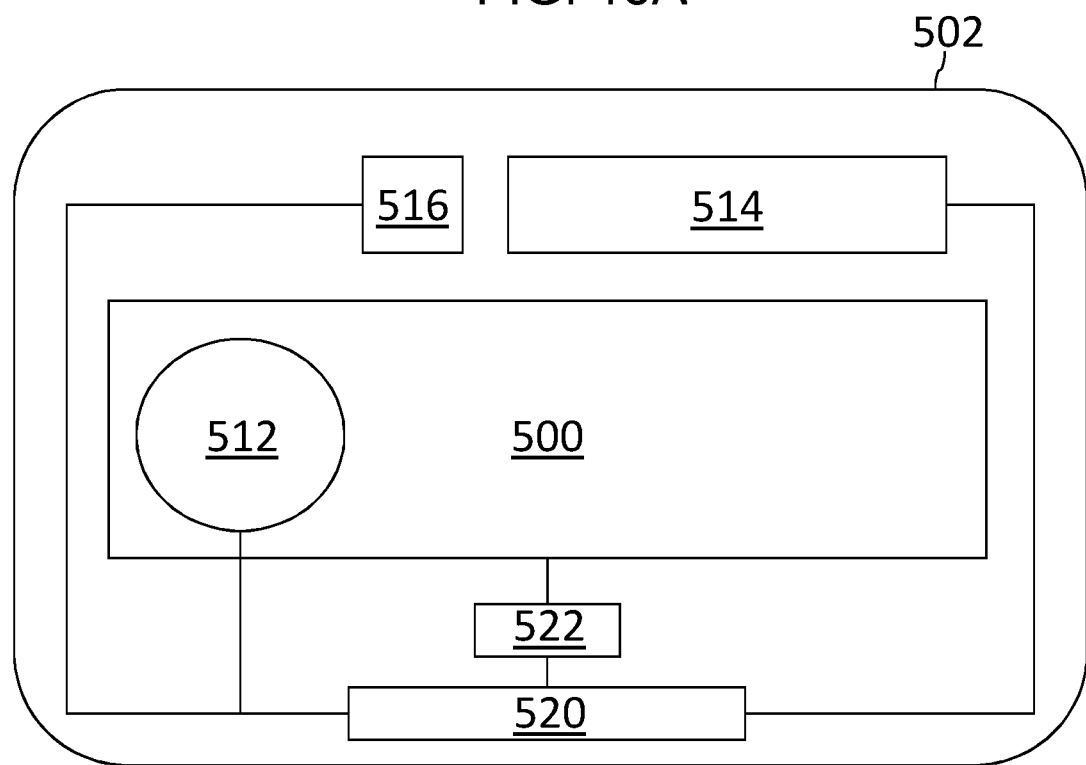
FIG. 13B shows a top schematic view of the actuatable assembly of FIG. 13A.

FIG. 13B is a top schematic view of the actuatable assembly 130 of FIG. 11A. The drive mechanism 500, encased within the housing 502 as described herein, comprises an electric motor 512 configured to drive the operation of one or more movable members of the mecanism. The actuatable assembly may further comprise a main control board 520, a processing unit operably coupled with the motor 512 and programmed with instructions to control operation of the motor. The main control board 520 may draw power from a battery 514 and/or an external power supply connector 516 configured to connect to, and draw power from, an external power supply. The main control board 520 may be in communication with, and configured to receive user operation commands through, the physical user interface 504 located on the outer surface of the housing. The main control board 520 may further be in communication with a software user interface of a computing device, for example via a wireless communication module (e.g., Bluetooth module) provided with the main control board. The actuatable assembly may further comprise a sensor board 522 operably coupled to the drive mechanism 500 and configured to sense a position of a movable member of the drive mechanism. The sensor board may be in communication with the main control board 520 to provide drive mechanism positional information to the main control board, wherein in the information may be used in controlling operation of the motor to adjust the position of the drive mechanism (e.g., return the mechanism to a "home" position).

Figure 13C:
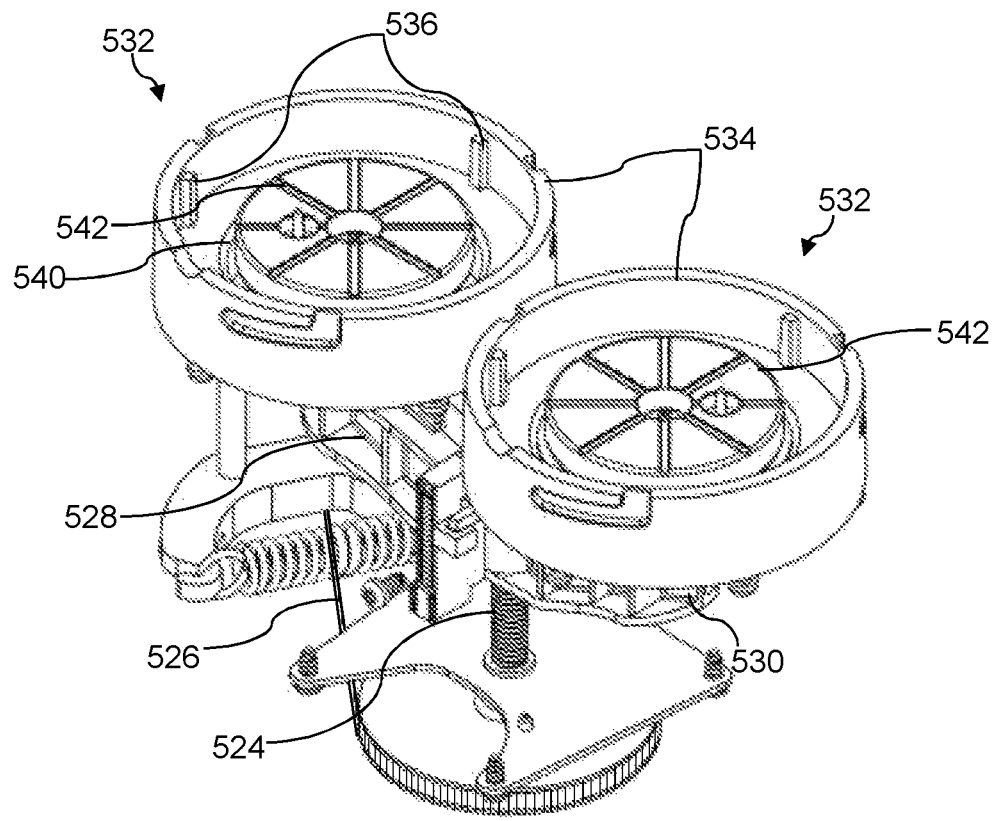
FIG. 13C shows an isometric view of an exemplary drive mechanism suitable for incorporation with an actuatable assembly.
Figure 13D:
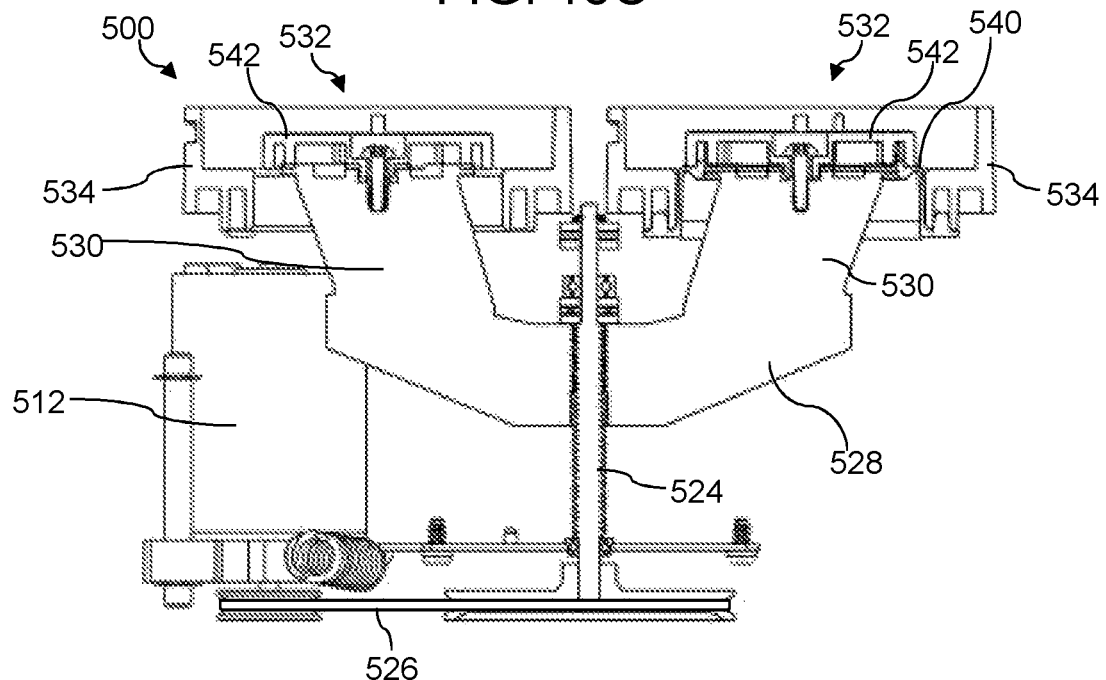
FIG. 13D shows a side cross-sectional view of the drive mechanism of FIG. 13C.
Figure 13E:
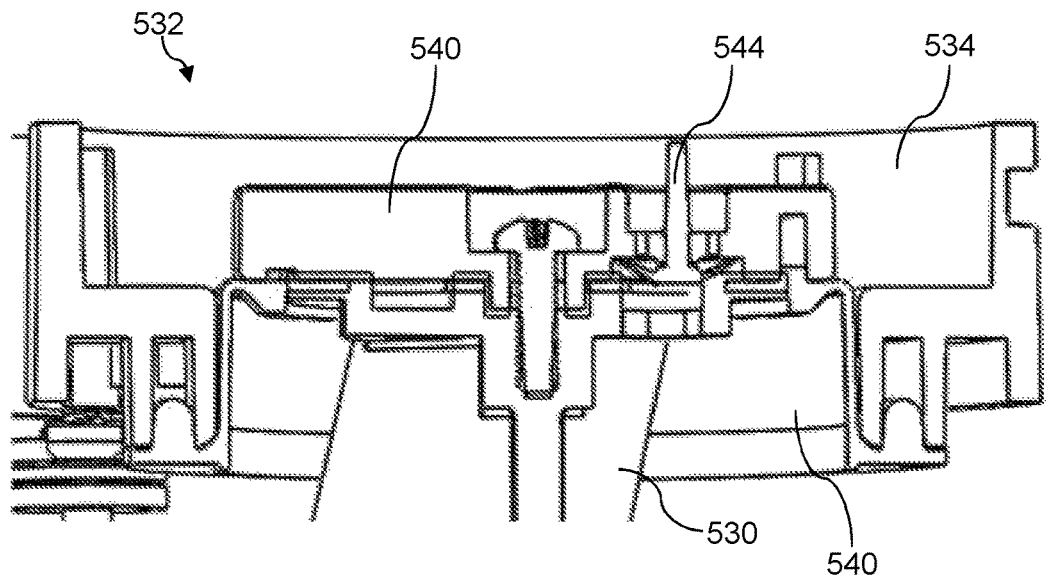
FIG. 13E shows a detailed side cross-sectional view of the BSA interface of FIG. 13A.

FIGS. 13C-13E illustrate an exemplary drive mechanism suitable for incorporation with any actuatable assembly as described herein. FIG. 13C is an isometric view, and FIG. 13D a side cross-sectional view of the drive mechanism 500. The drive mechanism 500 comprises a motor 512 in communication with the main control board of the actuatable assembly, as described herein. In the embodiment shown in FIGS. 13C and 13D, the motor 512 is a rotary motor operably coupled to a lead screw 524 via a belt 526. The lead screw 524 threadably engages carriage 528, such that when the lead screw rotates in response to actuation of the rotary motor 512, the carriage moves up or down accordingly. The carriage 528 may comprise two arms 530 disposed symmetrically about the lead screw, each arm coupled to a breast shield assembly (BSA) interface 532. Each BSA interface 532 is configured to physically and operably couple to an AAI of a breast shield assembly.

Each BSA interface 532 may comprise a locking portion 534 configured to removably and lockingly couple to an AAI of a breast shield assembly. The locking portion 534 may comprise one or more features to ensure proper alignment of the AAI during coupling of the AAI to the actuatable assembly, such as one or more ribs 536 configured to engage one or more corresponding rib slots of the AAI housing. The locking portion 534 may further comprise one or more features to securely hold the AAI into a locked position, such as one or more cam paths 538 configured to receive one or more corresponding cam pins of the AAI housing.

Each BSA interface 532 may further comprise an actuatable assembly (AA) membrane 540, captured between the top surface of the carriage arm 530 and a spacing member 542 (as best seen in FIG. 13E, showing a detailed side cross-sectional view of the BSA interface 532). The AA membrane 540 may be configured to move up or down along with the carriage arm 530 when the motor of the actuatable assembly is actuated. Each BSA interface 532 may further comprise a one-way valve 544 extending through the spacer 542.

Figure 13F:
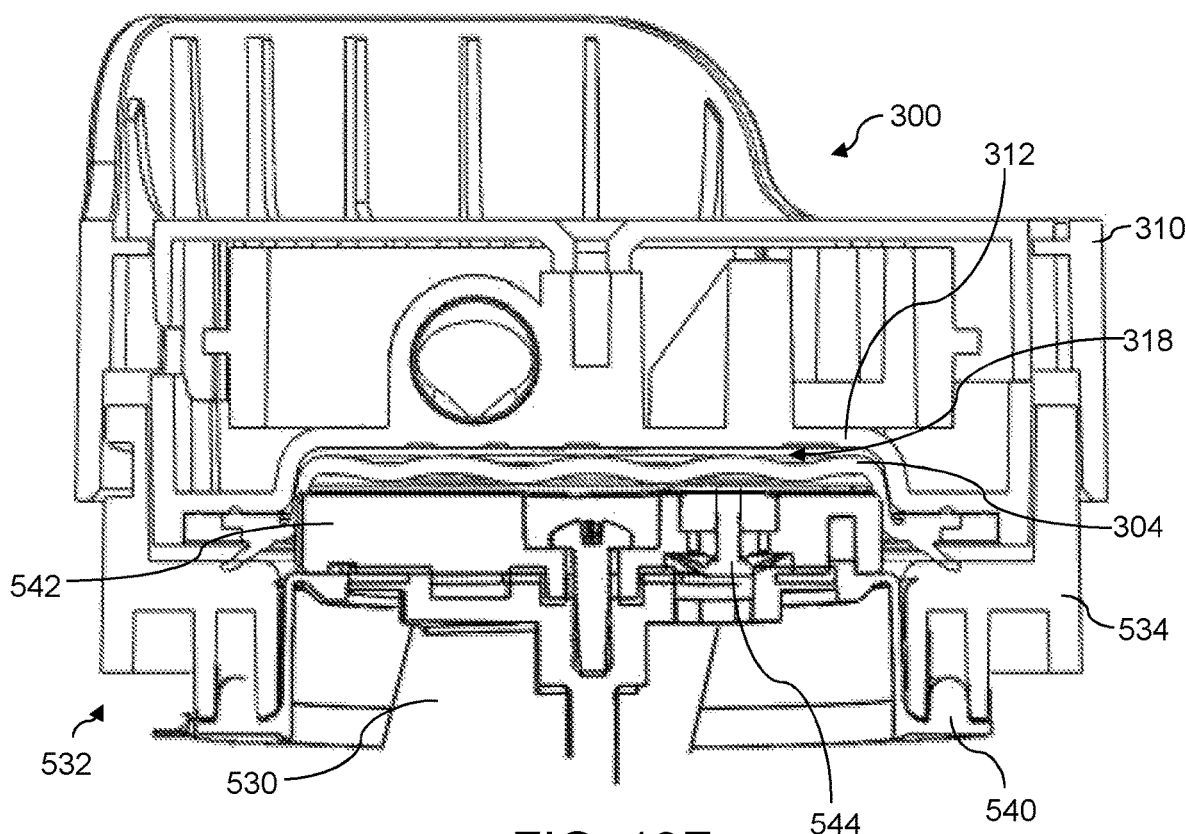
FIG. 13F shows a side cross-sectional view of the BSA interface of FIG. 13E coupled to an AAI of a breast shield assembly.

FIG. 13F is a side cross-sectional view of the BSA interface 532 of FIG. 13E coupled to an AAI 300 of a breast shield assembly as described herein. When the AAI 300 is locked onto the BSA interface 532 and operably coupled thereto, the AA membrane 540 and the AAI membrane 304 are brought into communication with one another, with the spacing member 542 providing a pre-set separation distance between the two membranes. As the motor of the actuatable assembly is actuated, the carriage arm 530 pushes the AA membrane 540 upward toward the AAI membrane 304, causing at least a portion of the air trapped between the two membranes to be pushed out via the one-way valve 544. Once the trapped air is pushed out through the valve outlet, the AAI membrane 304 becomes operably coupled to the AA membrane 504, such that the AAI membrane 304 will follow the cyclical motions of the AA membrane 504 as the actuatable assembly is actuated. Movement of the AAI membrane 304 away from or towards the AAI base 312 can cause the gap space 318 to increase or decrease in volume, in turn causing driving fluid to move into or out of the gap space. Corresponding movement of the driving fluid along with tube can cause movement of the breast interface membrane as described herein, thus generating negative pressure at the breast interface for expressing milk from the breast.

Figure 14:
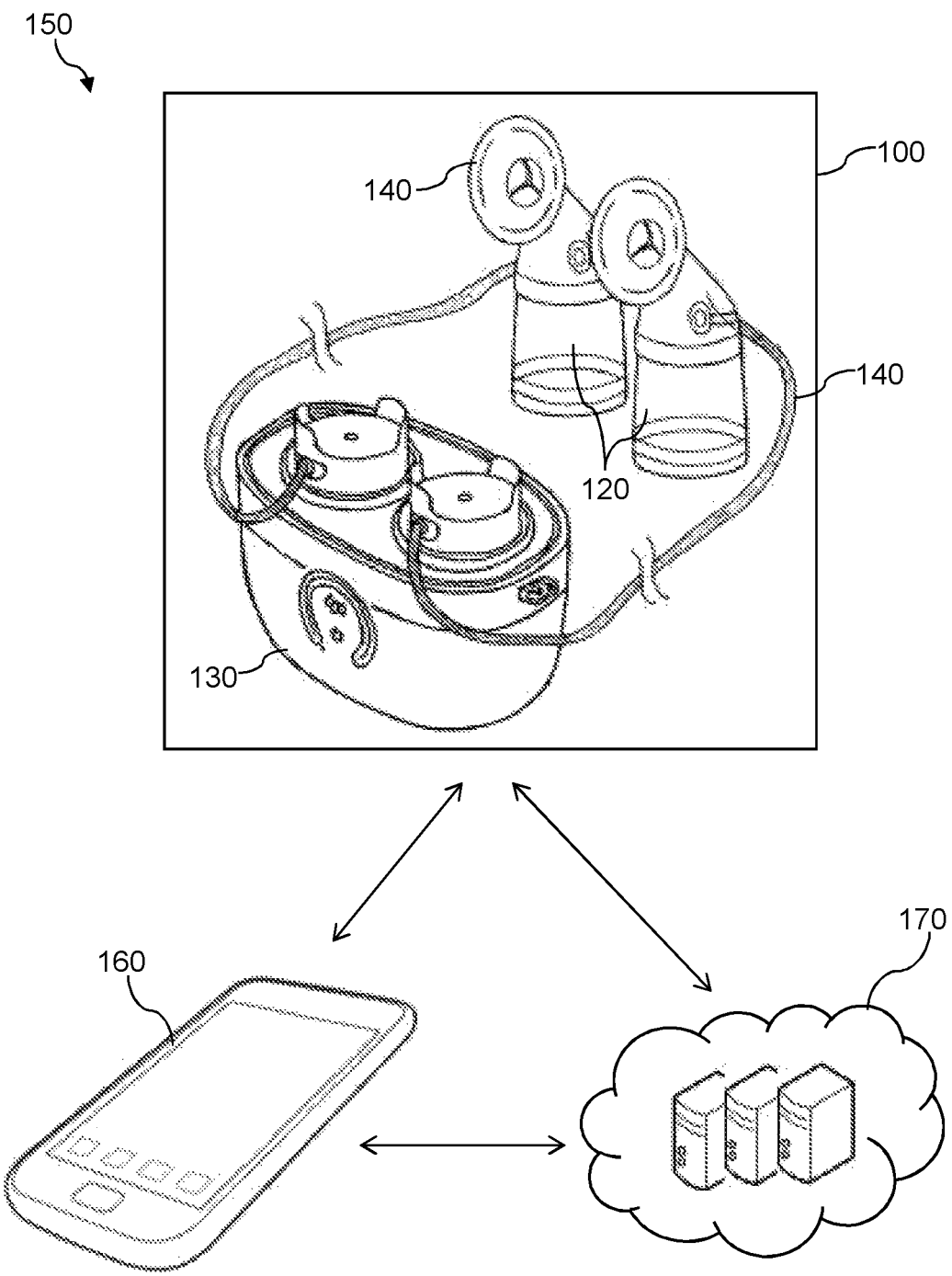
FIG. 14 illustrates an exemplary system for the expression of breast milk.

FIG. 14 illustrates an exemplary system 150 for the expression of breast milk in accordance with embodiments. The system 150 comprises a breast milk expression system 100, and a computing device such as a mobile communication device 160 in communication with the expression system 100. The expression system 100 may comprise an actuatable assembly 130, one or more breast shield assemblies 140, and one or more collection containers 120 as described herein. The mobile device 160 may be configured to communicate with one or more portions of the expression system 100, for example via near-field communication (e.g., Bluetooth). For example, the mobile device may be in communication with the main control board of the actuatable assembly as decribed herein, and/or with other processing units coupled to the actuatable assembly, breast shield assembly, and/or collection containers 120. The system 150 may further comprise a remote server 170 configured to communicate with one or more mobile devices 160. Optionally, the remote server 170 may further be configured to communicate directly with any portion of the expression system 100. The remote server may be configured to receive and store data from the mobile device and/or the expression system. Optionally, the server may be further configured to perform data analysis, and send analyzed data back to the mobile device for display to the user.

The mobile device 160 may be provided with a software user interface to control operation of one or more components of the expression system 100. For example, the mobile device may be provided with a mobile application configured to receive user operational commands, and transmit the commands to the main control board of the actuatable assembly. The software user interface may mirror the functions of the physical user interface provided with the actuatable assembly. The software user interface may also provide additional functions for controlling the operation of the expression system. For example, the user interface may enable a user to change a default operational setting for the pump, such as a default cycling frequency of the actuatable assembly in a specific operational mode, or the default duration of one operational mode.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus for expression of breast milk from a breast, the apparatus comprising:
   a breast shield assembly comprising a breast interface and an actuatable assembly interface fluidly coupled with a tube, the breast interface configured to engage the breast and the actuatable assembly interface configured to removably couple to an actuatable assembly,
   wherein the breast shield assembly comprises an enclosed fluid reservoir extending between the breast interface and the actuatable assembly interface, the fluid reservoir physically separated from the breast milk expressed from the breast and filled with a driving fluid comprising a liquid, the fluid reservoir configured within a portion of the breast interface and including an outer surface configured to engage the breast, and
   wherein the breast shield assembly comprises a fill port configured to allow addition or removal of the driving fluid to or from the fluid reservoir, the fill port positioned in a wall of the fluid reservoir.

2. An apparatus as in claim 1, wherein the fluid reservoir comprises a first reservoir at the breast interface and a second reservoir at the actuatable assembly interface, the first reservoir and the second reservoir in fluid communication with one another via the tube.

3. An apparatus as in claim 1, wherein the breast interface comprises the fill port.

4. An apparatus as in claim 3, wherein the breast interface is shaped to form a first opening to receive the breast therethrough, a second opening to couple to a collection container, a third opening to couple to the tube, and a fourth opening defining the fill port.

5. An apparatus as in claim 4, wherein the fill port is positioned at a portion of the breast interface that protrudes maximally in any one direction.

6. An apparatus as in claim 1, wherein the actuatable assembly interface comprises the fill port.

7. An apparatus as in claim 1, wherein the breast shield assembly comprises two or more fill ports, and wherein the breast interface comprises at least one of the two or more fill ports, and the actuatable assembly interface comprises at least one of the two or more fill ports.

8. An apparatus as in claim 1, further comprising a fill port plug configured to removably couple to the fill port so as to form a fluid-tight seal between the fill port plug and the fill port.

9. An apparatus as in claim 8, wherein the fill port plug is tethered to the breast shield assembly.

10. An apparatus as in claim 8, wherein the fill port plug comprises a flexible material.

11. An apparatus as in claim 8, wherein the fill port plug comprises a cover portion and a plug portion, the cover portion configured to extend over the fill port along an outer surface of the breast interface or the actuatable assembly interface, and the plug portion configured to fit through the fill port, wherein the cover portion has an outer diameter that is greater than a diameter of the fill port.

12. An apparatus as in claim 11, wherein the plug portion comprises an intermediate portion sized to fit snugly within the fill port and form a fluid-tight seal against an inner wall of the fill port, and an annular lip having an outer diameter that is greater than an outer diameter of the intermediate portion and greater than the diameter of the fill port.

13. An apparatus as in claim 12, wherein an inner surface of the plug portion defines a recessed central region surrounded by the annular lip, the recessed central region configured to allow the annular lip to flex radially outwards in response to inward pull forces exerted on the fill port plug.

14. An apparatus as in claim 1, further comprising an antimicrobial component in contact with the driving fluid, the antimicrobial component configured to reduce microbial growth in the driving fluid.

15. An apparatus as in claim 14, wherein the antimicrobial component comprises a copper alloy, copper, brass, bronze, silver, an antimicrobial polymer, polymeric biocides, or a combination thereof.

16. An apparatus as in claim 14, wherein the antimicrobial component is coupled to an inner surface of the tube.

17. A method of expressing breast milk from a breast, the method comprising:
   providing a breast shield assembly comprising a breast interface configured to engage the breast and an actuatable assembly interface configured to removably couple to an actuatable assembly, the breast shield assembly comprising an enclosed fluid reservoir extending between the breast interface and the actuatable assembly interface and configured within a portion of the breast interface and including an outer surface configured to engage the breast;
   adding a liquid driving fluid to the fluid reservoir through a fill port of the breast shield assembly, the fill port positioned in a wall of the fluid reservoir;
   engaging the breast with the breast interface;
   coupling the actuatable assembly interface to the actuatable assembly; and
   actuating the actuatable assembly to express the breast milk from the breast.

18. An apparatus for expression of breast milk from a breast, the apparatus comprising:
   a breast interface configured to engage and fluidly seal against the breast, the breast interface comprising a housing and a membrane coupled to the housing to form a fluid reservoir therebetween, the membrane including a portion defining a tube-like structure configured within a portion of the breast interface, the membrane configured to engage a breast, the fluid reservoir filled with a driving fluid comprising a liquid, and including a fill port positioned in a wall of the fluid reservoir,
   wherein the breast interface comprises a coupling portion configured to couple to a collection container while fluidly isolating the collection container from the fluid reservoir, and
   wherein the coupling portion comprises one or more venting features configured to provide an air gap between the collection container and the coupling portion, thereby allowing an internal volume of the collection container to vent to atmospheric pressure.

19. An apparatus as in claim 18, wherein the one or more venting features comprise one or more protruding ribs protruding from a bottom surface of the coupling portion, the one or more protruding ribs configured to partially contact a top surface of the collection container when the collection container is coupled to the breast interface, thus providing one or more air gaps between the collection container and the coupling portion.

20. An apparatus as in claim 19, wherein the coupling portion is further shaped to form an annular lip disposed closer to a center of the coupling portion than the one or more protruding ribs, the annular lip protruding past the one or more protruding ribs so as to reduce splashing of expressed breast milk towards the one or more air gaps.

\* \* \* \* \*